(12) United States Patent
Kato et al.

(10) Patent No.: US 8,642,806 B2
(45) Date of Patent: Feb. 4, 2014

(54) SQUARYLIUM COMPOUND, METHOD FOR PRODUCING THE SAME AND INFRARED ABSORBENT

(75) Inventors: Shunya Kato, Ashigarakami-gun (JP); Yoshihiro Jimbo, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 510 days.

(21) Appl. No.: 13/072,176

(22) Filed: Mar. 25, 2011

(65) Prior Publication Data

US 2011/0245538 A1  Oct. 6, 2011

(30) Foreign Application Priority Data

Mar. 30, 2010 (JP) ................................. 2010-079881

(51) Int. Cl.
*C07F 5/02* (2006.01)
(52) U.S. Cl.
USPC ............................................................ 564/11
(58) Field of Classification Search
USPC ............................................................ 564/11
See application file for complete search history.

(56) References Cited

FOREIGN PATENT DOCUMENTS

| | | |
|---|---|---|
| JP | 10-036695 A | 2/1989 |
| JP | 2000-159776 A | 6/2000 |
| JP | 2009-209297 A | 9/2009 |

*Primary Examiner* — Johann R Richter
*Assistant Examiner* — Kofi Adzamli
(74) *Attorney, Agent, or Firm* — Sughrue Mion, PLLC

(57) ABSTRACT

Provide is a compound having absorbability in an infrared region, excellent invisibility and robustness. The compound is a squarylium compound represented Formula (1):

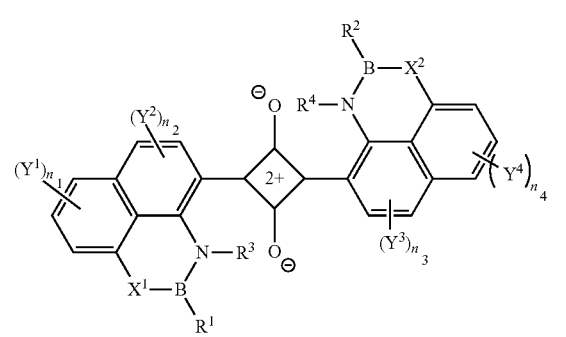

(1)

wherein, $R^1$ and $R^2$ represent an alkyl group, cycloalkyl group, aryl group, or heteroaryl group, which may be substituted by a substituent; $R^3$ and $R^4$ represent a hydrogen atom or alkyl group; $X^1$ and $X^2$ represent an oxygen atom or $-NR^5-$, in which $R^5$ represents a hydrogen atom or alkyl group; $Y^1$, $Y^2$, $Y^3$ and $Y^4$ represent a halogen atom, alkyl group, cycloalkyl group, aryl group, heteroaryl group, arylcarbonyloxy group, or alkylcarbonyloxy group; a plurality of $Y^1$'s, $Y^2$'s, $Y^3$'s, or $Y^4$'s may be bonded to form a ring structure, respectively; $Y^1$ and $Y^2$, or $Y^3$ and $Y^4$ may be bonded to form a ring structure; $n_1$ and $n_4$ represent an integer of 0 to 3; and $n_2$ and $n_3$ represent an integer of 0 to 2.

11 Claims, 1 Drawing Sheet

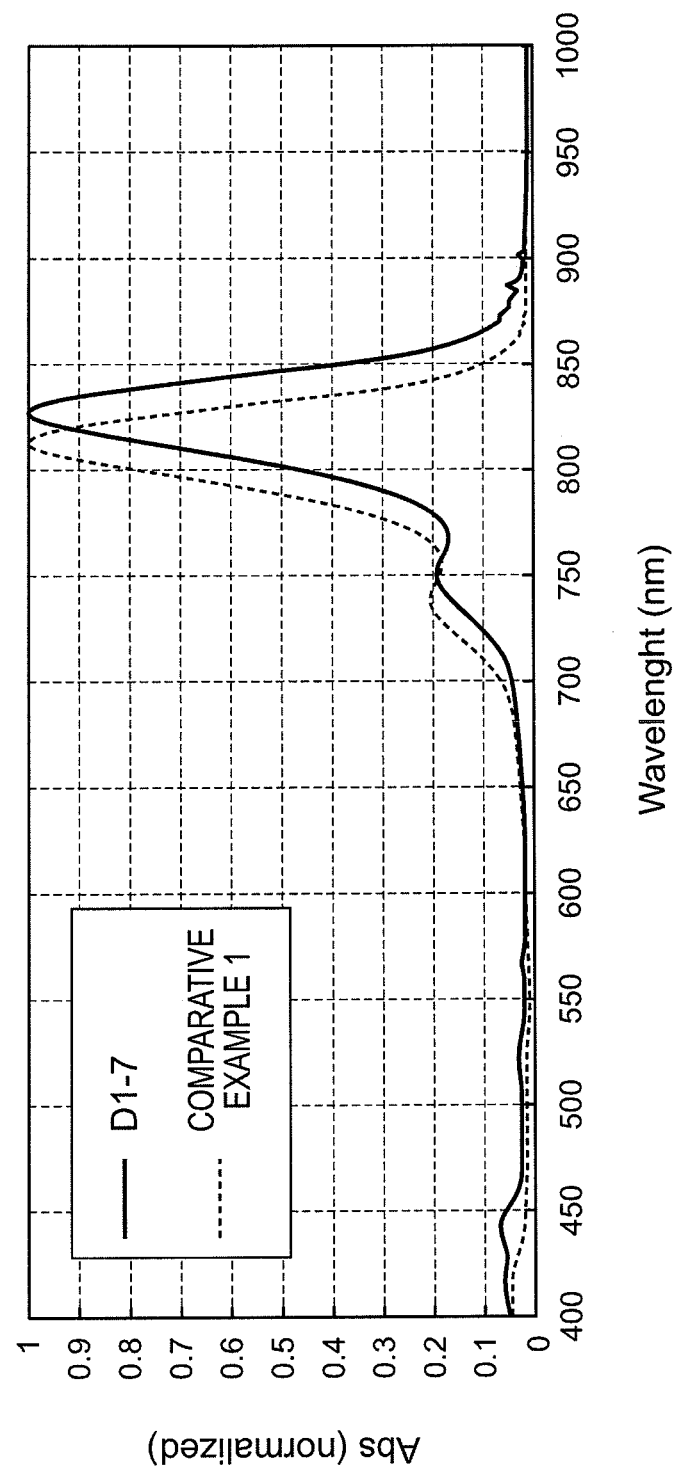

SQUARYLIUM COMPOUND, METHOD FOR PRODUCING THE SAME AND INFRARED ABSORBENT

CROSS-REFERENCE TO RELATED APPLICATION

This application claims priority under 35 USC 119 from Japanese Patent Application No. 2010-079881 filed on Mar. 30, 2010, the disclosure of which is incorporated by reference herein.

BACKGROUND OF THE INVENTION

1. Field of the Invention

The present invention relates to a novel squarylium compound, a method for producing the same and an infrared absorbent.

2. Description of the Related Art

Near-infrared absorbents are utilized in a variety of applications including optical films such as infrared ray cut films or heat ray shielding films for plasma display panels or charge coupled devices (CCDs), photothermal conversion materials for recordable optical discs or flash welding development materials, information display materials for security inks or invisible bar code inks. As for required performance characteristics, these infrared absorbents should exhibit high absorbability to infrared light or an infrared region, while exhibiting as low an absorbability to a visible region as possible (invisibility). In addition, robustness is required.

At present, cyanine methine pigments are provided as infrared absorbing pigments with superior invisibility. However, long methine conjugated chains readily react with heat, oxygen, nucleophiles and the like and are decomposed, and are generally considered to exhibit low robustness. Meanwhile, vanadylphthalocyanine pigments are provided as pigments with high robustness. However, the vanadylphthalocyanine pigments have insufficient invisibility. Accordingly, infrared absorbents exhibiting both invisibility and robustness have been required for a long period of time.

Recently, a squarylium compound has been provided as a material satisfying these requirements (Japanese Patent Application Laid-Open (JP-A) Nos. 2000-159776 and 10-36695). This squarylium compound exhibits excellent infrared absorbability, invisibility and robustness.

Meanwhile, when a compound having a higher wavelength range of absorption region (infrared region) is provided, a receiver can widely select an absorption wavelength range of infrared absorbing materials suitable for applications or products.

SUMMARY OF THE INVENTION

It is an object of the present invention to provide an infrared absorbing material with superior invisibility and robustness, which exhibits absorbability in an infrared region and has absorption peaks in a higher wavelength region.

As a result of intensive research, based on the object, the present inventors discovered that absorption peaks are shifted to a higher wavelength range by using a specific boron atom-containing squarylium compound obtained by introducing a boron atom to a conventional squarylium compound. The object was achieved based on the discovery. That is, the present invention relates to boron atom-containing squarylium, a method for preparing the same and an infrared absorbent.

<1> A squarylium compound represented by the following Formula (1):

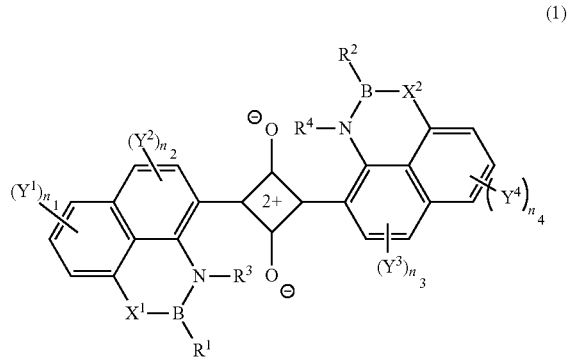

wherein, in Formula (1), $R^1$ and $R^2$ each independently represent an alkyl group having 1 to 12 carbon atoms, a cycloalkyl group having 3 to 6 carbon atoms, an aryl group of which the number of ring-forming atoms is from 5 to 14, or a heteroaryl group of which the number of ring-forming atoms is from 5 to 14;

wherein the alkyl group, cycloalkyl group, aryl group, and heteroaryl group may independently be substituted by an alkyl group having 1 to 8 carbon atoms, an alkoxy group having 1 to 8 carbon atoms, a hydroxyl group, a carboxyl group, a carbamoyl group, a halogen atom, an alkyloxycarbonyl group having 2 to 7 carbon atoms, an aryloxycarbonyl group having 7 to 11 carbon atoms, an alkylcarbonyloxy having 2 to 7 carbon atoms, an arylcarbonyloxy group having 7 to 11 carbon atoms, an alkylcarbamoyl group having 2 to 7 carbon atoms, or an arylcarbamoyl group having 7 to 11 carbon atoms;

$R^3$ and $R^4$ each independently represent a hydrogen atom or an alkyl group having 1 to 4 carbon atoms;

$X^1$ and $X^2$ each independently represent an oxygen atom or —$NR^5$—, in which $R^5$ represents a hydrogen atom or an alkyl group having 1 to 4 carbon atoms;

$Y^1$, $Y^2$, $Y^3$ and $Y^4$ each independently represent a halogen atom, an alkyl group having 1 to 6 carbon atoms, a cycloalkyl group having 4 to 6 carbon atoms, an aryl group of which the number of ring-forming atoms is from 5 to 14, a heteroaryl group of which the number of ring-forming atoms is from 5 to 14, an arylcarbonyloxy group of which the number of ring-forming atoms is from 5 to 14, or an alkylcarbonyloxy group having 2 to 7 carbon atoms;

when a plurality of $Y^1$'s is present, the plurality of $Y^1$'s may be bonded to each other to form a ring structure;

when a plurality of $Y^2$'s is present, the plurality of $Y^2$'s may be bonded to each other to form a ring structure;

when a plurality of $Y^3$'s is present, the plurality of $Y^3$'s may be bonded to each other to form a ring structure;

when a plurality of $Y^4$'s is present, the plurality of $Y^4$'s may be bonded to each other to form a ring structure;

$Y^1$ and $Y^2$ may be bonded to each other to form a ring structure;

$Y^3$ and $Y^4$ may be bonded to each other to form a ring structure;

$n_1$ and $n_4$ each independently represent an integer of from 0 to 3; and $n_2$ and $n_3$ each independently represent an integer of from 0 to 2.

<2> The squarylium compound according to <1>, wherein $R^3$ and $R^4$ each independently represent a hydrogen atom or a methyl group.

<3> The squarylium compound according to <1>, wherein $n_1$, $n_2$, $n_3$ and $n_4$ each represent zero.

<4> The squarylium compound according to <1>, wherein $X^1$ and $X^2$ each represent an oxygen atom.

<5> The squarylium compound according to <1>, wherein $X^1$ and $X^2$ each represent —NH— or —$NCH_3$—.

<6> A microparticle including the squarylium compound according to <1>.

<7> A coating composition including the microparticle according to <6>.

<8> An infrared absorbent including the squarylium compound represented by the following Formula (1A):

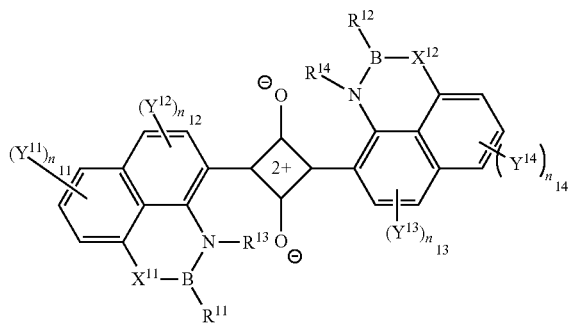

(1A)

wherein, in Formula (1A), $R^{11}$ and $R^{12}$ each independently represent a substituted or unsubstituted alkyl group, a substituted or unsubstituted cycloalkyl group, a substituted or unsubstituted aryl group, or a substituted or unsubstituted heteroaryl group;

$R^{13}$ and $R^{14}$ each independently represent a hydrogen atom or a substituted or unsubstituted alkyl group;

$X^{11}$ and $X^{12}$ each independently represent an oxygen atom or —$NR^{15}$—, in which $R^{15}$ represents a hydrogen atom or a substituted or unsubstituted alkyl group;

$Y^{11}$, $Y^{12}$, $Y^{13}$ and $Y^{14}$ each independently represent a halogen atom, a substituted or unsubstituted alkyl group, a substituted or unsubstituted cycloalkyl group, a substituted or unsubstituted aryl group, a substituted or unsubstituted heteroaryl group, a substituted or unsubstituted arylcarbonyloxy group, or a substituted or unsubstituted alkylcarbonyloxy group;

when a plurality of $Y^{11}$'s is present, the plurality of $Y^{11}$'s may be bonded to each other to form a ring structure;

when a plurality of $Y^{12}$'s is present, the plurality of $Y^{12}$'s may be bonded to each other to form a ring structure;

when a plurality of $Y^{13}$'s is present, the plurality of $Y^{13}$'s may be bonded to each other to form a ring structure;

when a plurality of $Y^{14}$'s is present, the plurality of $Y^{14}$'s may be bonded to each other to form a ring structure;

$Y^{11}$ and $Y^{12}$ may be bonded to each other to form a ring structure;

$Y^{13}$ and $Y^{14}$ may be bonded to each other to form a ring structure;

$n_{11}$ and $n_{14}$ each independently represent an integer of from 0 to 3; and $n_{12}$ and $n_{13}$ each independently represent an integer of from 0 to 2.

<9> A method for producing a squarylium compound represented by the following Formula (1):

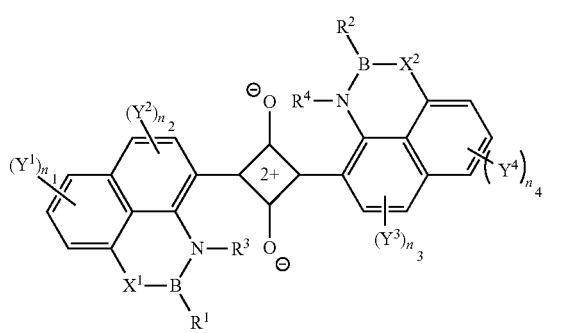

(1)

wherein, in Formula (1), $R^1$ and $R^2$ each independently represent an alkyl group having 1 to 12 carbon atoms, a cycloalkyl group having 3 to 6 carbon atoms, an aryl group of which the number of ring-forming atoms is from 5 to 14, or a heteroaryl group of which the number of ring-forming atoms is from 5 to 14;

wherein the alkyl group, cycloalkyl group, aryl group, and heteroaryl group may independently be substituted by an alkyl group having 1 to 8 carbon atoms, an alkoxy group having 1 to 8 carbon atoms, a hydroxyl group, a carboxyl group, a carbamoyl group, a halogen atom, an alkyloxycarbonyl group having 2 to 7 carbon atoms, an aryloxycarbonyl group having 7 to 11 carbon atoms, an alkylcarbonyloxy group having 2 to 7 carbon atoms, an arylcarbonyloxy group having 7 to 11 carbon atoms, an alkylcarbamoyl group having 2 to 7 carbon atoms, or an arylcarbamoyl group having 7 to 11 carbon atoms;

$R^3$ and $R^4$ each independently represent a hydrogen atom or an alkyl group having 1 to 4 carbon atoms;

$X^1$ and $X^2$ each independently represent an oxygen atom or —$NR^5$—, in which $R^5$ represents a hydrogen atom or an alkyl group having 1 to 4 carbon atoms;

$Y^1$, $Y^2$, $Y^3$ and $Y^4$ each independently represent a halogen atom, an alkyl group having 1 to 6 carbon atoms, a cycloalkyl group having 4 to 6 carbon atoms, an aryl group of which the number of ring-forming atoms is from 5 to 14, a heteroaryl group of which the number of ring-forming atoms is from 5 to 14, an arylcarbonyloxy group of which the number of ring-forming atoms is from 5 to 14, or an alkylcarbonyloxy group having 2 to 7 carbon atoms;

when a plurality of $Y^1$'s is present, the plurality of $Y^1$'s may be bonded to each other to form a ring structure;

when a plurality of $Y^2$'s is present, the plurality of $Y^2$'s may be bonded to each other to form a ring structure;

when a plurality of $Y^3$'s is present, the plurality of $Y^3$'s may be bonded to each other to form a ring structure;

when a plurality of $Y^4$'s is present, the plurality of $Y^4$'s may be bonded to each other to form a ring structure;

$Y^1$ and $Y^2$ may be bonded to each other to form a ring;

$Y^3$ and $Y^4$ may be bonded to each other to form a ring;

$n_1$ and $n_4$ each independently represent an integer of from 0 to 3; and $n_2$ and $n_3$ each independently represent an integer of from 0 to 2, the method including:

reacting a compound represented by the following Formula (2) and a compound represented by the following Formula (3) with squaric acid:

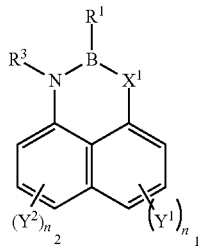

(2)

wherein, in Formula (2), $R^1$, $R^3$, $X^1$, $Y^1$, $Y^2$, $n_1$ and $n_2$ have the same definitions as those of Formula (1), respectively;

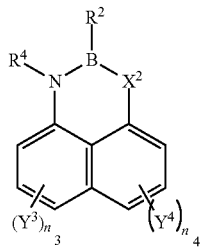

(3)

wherein, in Formula (3), $R^2$, $R^4$, $X^2$, $Y^3$, $Y^4$, $n_3$ and $n_4$ have the same definitions as those of Formula (1), respectively.

<10> The method according to <9>, wherein the compound represented by Formula (3) is the same as the compound represented by Formula (2).

<11> The method according to <9>, further including:

producing the compound represented by Formula (2) by reacting a boronic acid compound represented by the following Formula (5) with a 1,8-diaminonaphthalene compound or a 1-amino-8-hydroxynaphthalene compound:

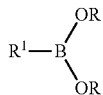

(5)

wherein, in Formula (5), $R^1$ has the same definition as that of Formula (2); and R's each independently represent a hydrogen atom, or an alkyl group having 1 to 3 carbon atoms, and R's may be bonded to each other to form a ring structure.

According to the present invention, provided is a compound which has infrared absorbability and exhibits superior invisibility and robustness.

BRIEF DESCRIPTION OF THE DRAWINGS

FIG. 1 is a graph showing measurement results of absorption spectra of squarylium compounds produced in Example 1 and Comparative Example 1.

DETAILED DESCRIPTION OF THE INVENTION

1. Squarylium Compound

The squarylium compound according to the present invention is represented by the following Formula (1):

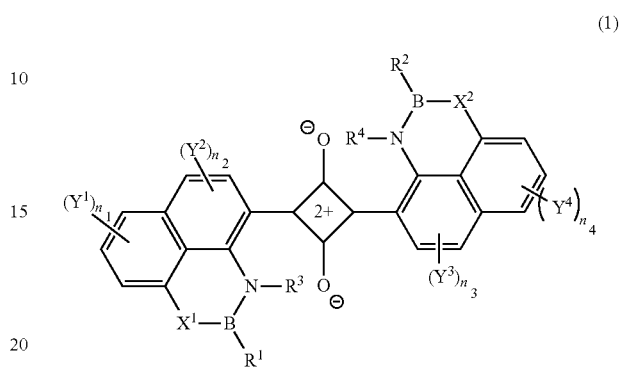

(1)

In Formula (1), $R^1$ and $R^2$ each independently represent an alkyl group having 1 to 12 carbon atoms, a cycloalkyl group having 3 to 6 carbon atoms, an aryl group of which the number of ring-forming atoms is from 5 to 14, or a heteroaryl group of which the number of ring-forming atoms is from 5 to 14, wherein the alkyl group, cycloalkyl group, aryl group, and heteroaryl group may be independently substituted by another substituent such as an alkyl group having 1 to 4 carbon atoms, an alkoxy group having 1 to 8 carbon atoms, a hydroxyl group, a carboxyl group, a carbamoyl group, a halogen atom, an alkyloxycarbonyl group having 2 to 7 carbon atoms, an aryloxycarbonyl group having 7 to 11 carbon atoms, an alkylcarbonyloxy group having 2 to 7 carbon atoms, an arylcarbonyloxy group having 7 to 11 carbon atoms, an alkylcarbamoyl group having 2 to 7 carbon atoms, or an arylcarbamoyl group having 7 to 11 carbon atoms;

$R^3$ and $R^4$ each independently represent a hydrogen atom or an alkyl group having 1 to 4 carbon atoms;

$X^1$ and $X^2$ each independently represent an oxygen atom or —$NR^5$—, in which $R^5$ represents a hydrogen atom or an alkyl group having 1 to 4 carbon atoms;

$Y^1$, $Y^2$, $Y^3$ and $Y^4$ each independently represent a halogen atom, an alkyl group having 1 to 4 carbon atoms, a cycloalkyl group having 4 to 6 carbon atoms, an aryl group of which the number of ring-forming atoms is from 5 to 10, a heteroaryl group of which the number of ring-forming atoms is from 5 to 10, an arylcarbonyloxy group of which the number of ring-forming atoms is from 5 to 10, or an alkylcarbonyloxy group having 2 to 7 carbon atoms;

wherein, when plural $Y^1$'s are present, plural $Y^1$'s may be bonded to each other to form a ring structure; when plural $Y^2$'s are present, plural $Y^2$'s may be bonded to each other to form a ring structure; when plural $Y^3$'s are present, plural $Y^3$'s may be bonded to each other to form a ring structure; when plural $Y^4$'s are present, plural $Y^4$'s may be bonded to each other to form a ring structure;

$Y^1$ and $Y^2$ may be bonded together to form a ring structure;

$Y^3$ and $Y^4$ may be bonded together to form a ring structure;

$n_1$ and $n_4$ each independently represent an integer of 0 to 3; and $n_2$ and $n_3$ each independently represent an integer of 0 to 2.

$R^1$ represents an alkyl group, a cycloalkyl group, an aryl group or a heteroaryl group. These groups each may have a substituent or may not have a substituent.

The alkyl group represented by $R^1$ is, for example, an alkyl group having 1 to 12 carbon atoms, and preferably an alkyl group having 1 to 8 carbon atoms. The alkyl group may be straight or branched. Specific examples thereof include a methyl group, an ethyl group, a propyl group, an isopropyl group, a butyl group, an isobutyl group, a pentyl group, a 2-methylbutyl group and 2-ethylhexyl group.

The cycloalkyl group represented by $R^1$ is, for example, a cycloalkyl group having 3 to 6 carbon atoms, and preferably a cycloalkyl group having 5 or 6 carbon atoms. The alkyl group branched from the ring of the cycloalkyl group may be straight or branched. Specific examples of the cycloalkyl group include a cyclopropyl group, a cyclobutyl group, a cyclopentyl group and a cyclohexyl group.

The number of atoms that forms the ring structure of the aryl group represented by $R^1$ is, for example, from 5 to 14, and is preferably from 5 to 10. The aryl group may be a monocyclic ring or a condensed ring. The aryl group is, for example, an aryl group having 5 to 14 carbon atoms, and preferably an aryl group having 5 to 10 carbon atoms. Specific examples of the aryl group include a benzene ring, a naphthalene ring, a phenanthrene ring and an anthracene ring.

The number of atoms that forms the ring structure of the heteroaryl group represented by $R^1$ is, for example, from 5 to 14, and is preferably from 5 to 10. The heteroaryl group may be a monocyclic ring or a condensed ring. Examples of the hetero atom include a nitrogen atom, an oxygen atom, and a sulfur atom. The heteroaryl group may have 4 to 13 carbon atoms, and preferably 4 to 9 carbon atoms. Specific examples of the heteroaryl group include a furan ring, a thiophene ring, a pyrrole ring, a pyridine ring, a pyrazine ring, a pyrimidine ring, a pyridazine ring, a quinoline ring, a quinoxaline ring, a quinazoline ring, an indole ring, a benzofuran ring, and a benzothiophene ring.

These groups represented by $R^1$ may each have one or more substituents. Examples of substituents include an alkyl groups having 1 to 8 carbon atoms, an alkoxy groups having 1 to 8 carbon atoms, a hydroxyl group, a carboxyl group, a carbamoyl group, a halogen atom, an alkyloxycarbonyl group having 2 to 7 carbon atoms, an aryloxycarbonyl group having 7 to 11 carbon atoms, an alkylcarbonyloxy group having 2 to 7 carbon atoms, an arylcarbonyloxy group having 7 to 11 carbon atoms, an alkylcarbamoyl groups having 2 to 7 carbon atoms and an arylcarbamoyl group having 7 to 11 carbon atoms. More preferred are an alkyl group having 1 to 4 carbon atoms, an alkoxy group having 1 to 4 carbon atoms, a hydroxyl group, a carboxyl group, a carbamoyl group and a halogen atom. When $R^1$ has such a substituent and the substituent contains at least one carbon atom, the number of carbon atoms in the substituent is not included in the number of carbon atoms of the alkyl group having 1 to 12 carbon atoms, cycloalkyl group having 3 to 6 carbon atoms, or aryl group or heteroaryl group of which the number of ring-forming atoms is from 5 to 14, which is represented by $R^1$. Hereinbelow, in the present invention, a method for counting carbon number when one or more substituents are present is the same as described above.

$R^2$ is an alkyl group, a cycloalkyl group, an aryl group or a heteroaryl group. These groups each may have a substituent or may not have a substituent. The alkyl group, the cycloalkyl group, the aryl group, the heteroaryl group and the substituent have the same definitions as those described for $R^1$ (including preferred examples).

In the present invention, $R^1$ and $R^2$ preferably represent the same group. $R^3$ represents a hydrogen atom or an alkyl group. The alkyl group represented by $R^3$ is, for example, an alkyl group having 1 to 4 carbon atoms, and preferably 1 or 2 carbon atoms. The alkyl group may be straight or branched. Specific examples of the alkyl group include a methyl group, an ethyl group, a propyl group, an isopropyl group, a butyl group and an isobutyl group. $R^3$ is preferably a hydrogen atom, a methyl group or an ethyl group, particularly preferably hydrogen or a methyl group, and most preferably is a hydrogen atom.

$R^4$ represents a hydrogen atom or an alkyl group, and has the same definition as that described for $R^3$ (including preferred examples).

In the present invention, $R^3$ and $R^4$ preferably represent the same group.

$X^1$ represents an oxygen atom (—O—) or —$NR^5$—, in which $R^5$ represents a hydrogen atom or an alkyl group having 1 to 4 carbon atoms. The alkyl group represented by $R^5$ has the same definition as that described for $R^3$ (including preferred examples).

$X^2$ represents an oxygen atom (—O—) or —$NR^5$—, in which $R^5$ represents a hydrogen atom or an alkyl group having 1 to 4 carbon atoms. The alkyl group represented by $R^5$ has the same definition as that described for $R^3$ (including preferred examples).

In the present invention, $X^1$ and $X^2$ preferably represent the same group.

$Y^1$ represents a halogen atom, an alkyl group, a cycloalkyl group, an aryl group, a heteroaryl group, an arylcarbonyloxy group, or an alkylcarbonyloxy group. These groups may each have a substituent or may not have a substituent.

Examples of the halogen atom include a fluorine atom, a chlorine atom and a bromine atom.

The alkyl group represented by $Y^1$ is, for example, an alkyl group having 1 to 6 carbon atoms, and preferably an alkyl group having 1 to 4 carbon atoms. The alkyl group may be straight or branched. Specific examples of the alkyl group include a methyl group, an ethyl group, a propyl group, an isopropyl group, a butyl group, an isobutyl group, a pentyl group, and a hexyl group.

The cycloalkyl group represented by $Y^1$ is, for example, a cycloalkyl group having 4 to 6 carbon atoms, and preferably a cycloalkyl group having 5 to 6 carbon atoms. The alkyl group branched from the ring of the cycloalkyl group may be straight or branched. Specific examples of the cycloalkyl group include a cyclobutyl group, a cyclopentyl group and a cyclohexyl group.

The number of atoms that forms the ring structure of the aryl group represented by $Y^1$ is, for example, from 5 to 14, and is preferably from 6 to 10. The aryl group may be a monocyclic or condensed ring. The aryl group is, for example, an aryl group having 5 to 14 carbon atoms, and preferably an aryl group having 6 to 10 carbon atoms. Specific examples of the aryl group include a benzene ring, a naphthalene ring, a phenanthrene ring, and an anthracene ring.

The number of atoms that forms the ring structure of the heteroaryl group represented by $Y^1$ is, for example, from 5 to 14, and is preferably from 5 to 10. The heteroaryl group may be a monocyclic or condensed ring. The heteroaryl group is, for example, a heteroaryl group having 4 to 13 carbon atoms, and preferably a heteroaryl group having 4 to 9 carbon atoms. Examples of the heteroatom include a nitrogen atom and a sulfur atom. Specific examples of the heteroaryl group include a furan ring, a thiophene ring, a pyrrole ring, a pyridine ring, a pyrazine ring, a pyrimidine ring, a pyridazine ring, a quinoline ring, a quinoxaline ring, a quinazoline ring, an indole ring, a benzofuran ring and a benzothiophene ring.

The number of atoms that forms the ring structure of the arylcarbonyloxy group represented by $Y^1$ is, for example, from 5 to 14, and is preferably from 6 to 10. The arylcarbonyloxy group may be a monocyclic or condensed ring. The carbon number of the aryl moiety of the arylcarbonyloxy group is, for example, from 6 to 14, and preferably from 6 to 10. Specific examples of the arylcarbonyloxy group include a phenylcarbonyloxy group and a naphthylcarbonyloxy group.

The carbon number of the alkyl group moiety in the alkylcarbonyloxy group represented by $Y^1$ is, for example, from 1 to 6, and is preferably from 1 to 5. The alkylcarbonyloxy group may be straight or branched. Specific examples of the alkylcarbonyloxy group include a methylcarbonyloxy group, an ethylcarbonyloxy group, a propylcarbonyloxy group and a 2-methylbutylcarbonyloxy group.

In Formula (1), $Y^2$, $Y^3$ and $Y^4$ each independently represent a halogen atom, or a substituted or unsubstituted alkyl group, a substituted or unsubstituted cycloalkyl group, a substituted or unsubstituted aryl group, a substituted or unsubstituted heteroaryl group, a substituted or unsubstituted alkylcarbonyloxy group or a substituted or unsubstituted arylcarbonyloxy group. These groups have the same definitions (including preferred examples) as those described for $Y^1$, respectively.

When there are plural $Y^1$'s, $Y^2$'s, $Y^3$'s or $Y^4$'s, $Y^1$'s, $Y^2$'s, $Y^3$'s or $Y^4$'s may be bonded together to form a ring structure, respectively. For example, when plural $Y^1$'s are present, the plural $Y^1$'s may be bonded to each other to form a ring, and may form, for example, a tricyclic ring such as anthracene ring or phenanthrene ring together with the naphthalene ring to which $Y^1$ and $Y^2$ are directly bonded. Alternatively, $Y^1$ and $Y^2$ may be bonded to each other and may form, for example, a tricyclic ring such as an acenaphthene or acenaphthylene ring together with the naphthalene ring to which $Y^1$ and $Y^2$ are directly bonded.

In Formula (1), $n_1$ and $n_4$ each represent an integer of from 0 to 3, preferably an integer of from 0 to 1, and particularly preferably 0. Furthermore, $n_2$ and $n_3$ each represent an integer of from 0 to 2, preferably an integer of from 0 to 1, and particularly preferably 0.

In the present invention, the squarylium compound is preferably represented by the following Formula (1a), and most preferably represented by the following Formula (1b).

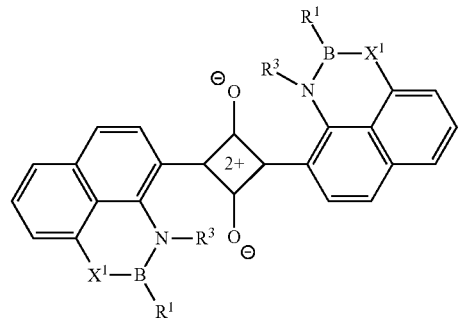

(1a)

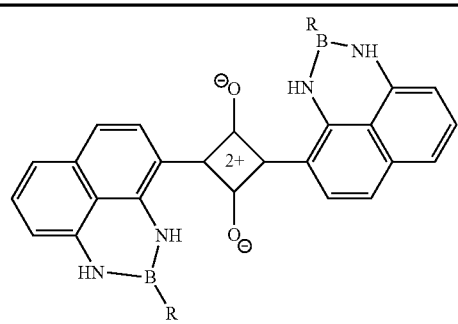

(1b)

Hereinafter, specific examples of the squarylium compound of the present invention will be shown, but the present invention is not limited to the following specific example.

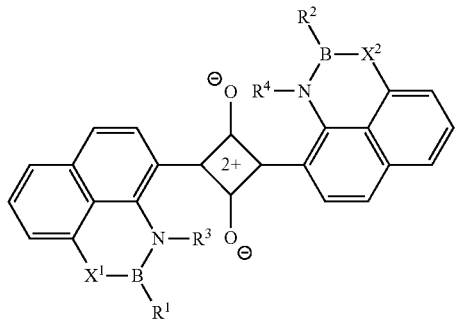

| R | No |
|---|---|
| Ph—* | D1-1 |
| Me—C6H4—* | D1-2 |
| tBu—C6H4—* | D1-3 |
| HO—C6H4—* | D1-4 |
| HOOC—C6H4—* | D1-5 |
| 2-pyridyl—* | D1-6 |
| 1-naphthyl—* | D1-7 |

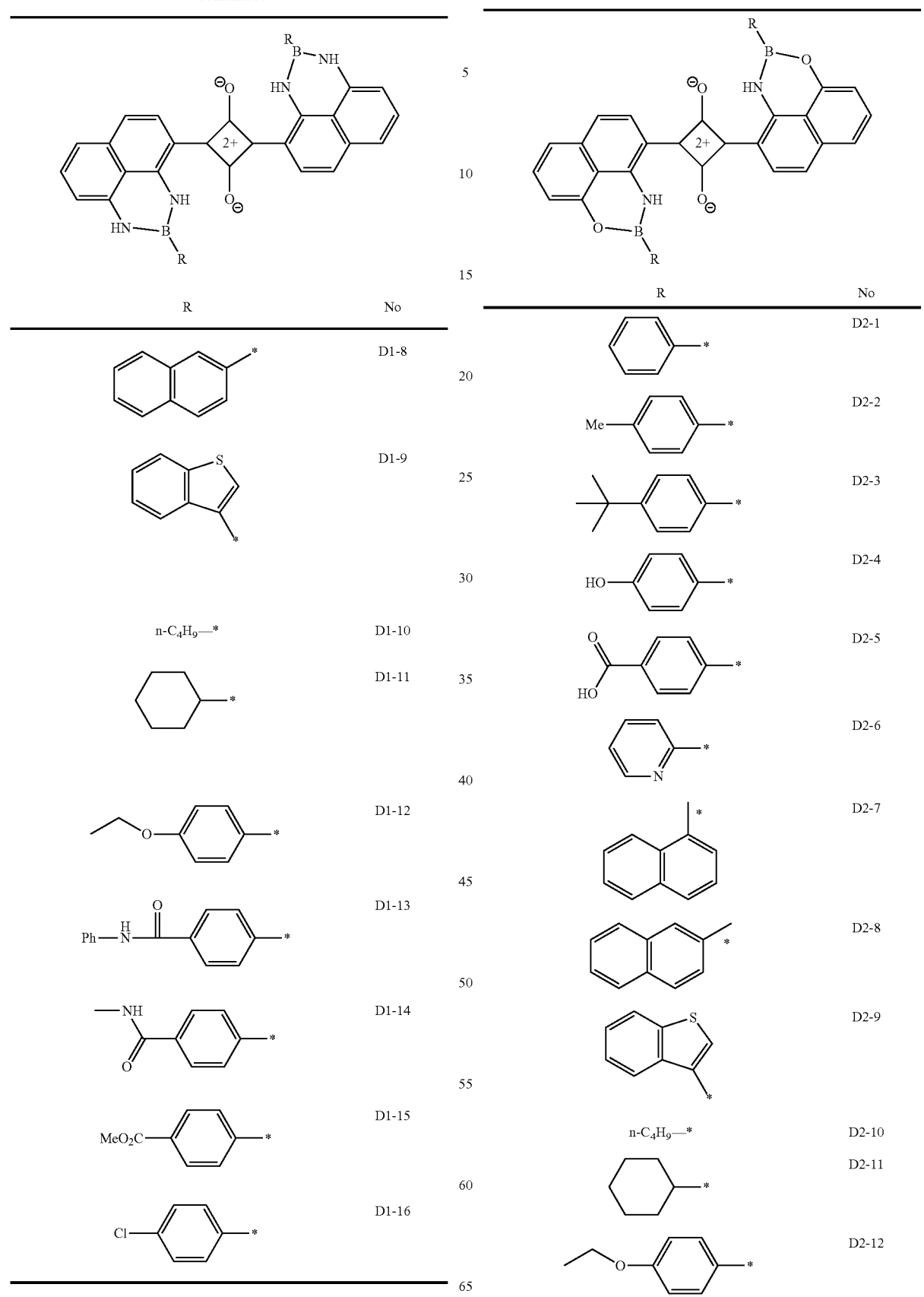

US 8,642,806 B2
13
-continued
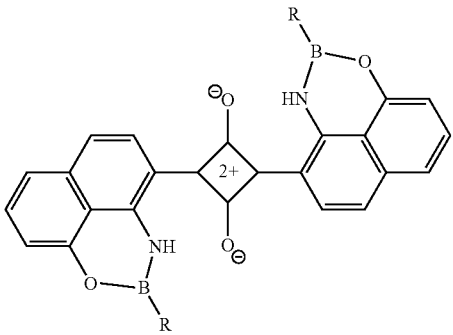
| R | No |
|---|---|
| 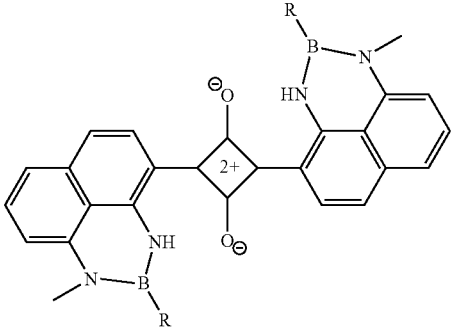 | D2-13 |
| 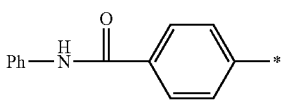 | D2-14 |
| 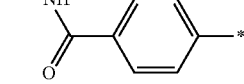 | D2-15 |
| 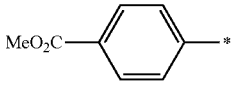 | D2-16 |
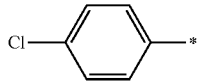
| R | No |
|---|---|
| 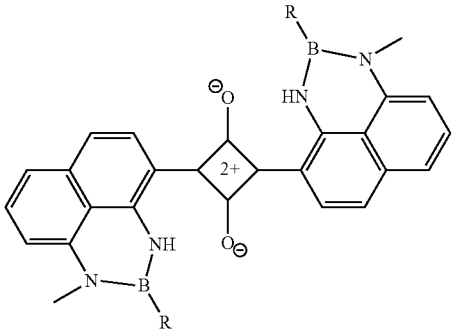 | D3-1 |
| 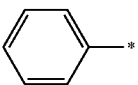 | D3-2 |
| 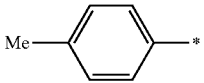 | D3-3 |
14
-continued
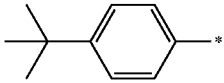
| R | No |
|---|---|
| 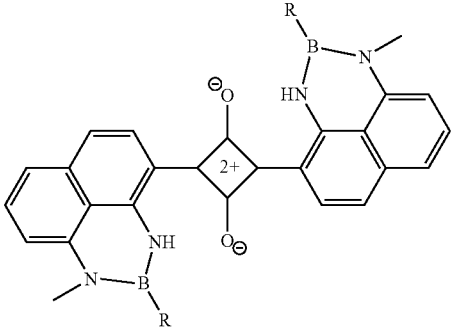 | D3-4 |
|  | D3-5 |
| 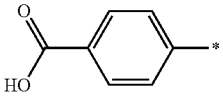 | D3-6 |
| 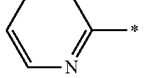 | D3-7 |
| 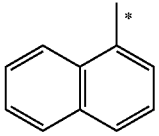 | D3-8 |
| 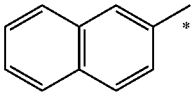 | D3-9 |
| n-C$_4$H$_9$—* | D3-10 |
| 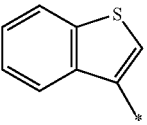 | D3-11 |
|  | D3-12 |
| 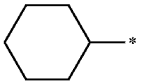 | D3-13 |
| 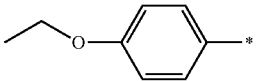 | D3-14 |

-continued

| R | No |
|---|---|
| 4-(MeO₂C)C₆H₄–* | D3-15 |
| 4-Cl-C₆H₄–* | D3-16 |

| R | No |
|---|---|
| C₆H₅–* (phenyl) | D4-1 |
| 4-Me-C₆H₄–* | D4-2 |
| 4-tBu-C₆H₄–* | D4-3 |
| 4-HO-C₆H₄–* | D4-4 |
| 4-(HO₂C)C₆H₄–* | D4-5 |
| 2-pyridyl–* | D4-6 |

-continued

| R | No |
|---|---|
| 1-naphthyl–* | D4-7 |
| 2-naphthyl–* | D4-8 |
| 3-benzothienyl–* | D4-9 |
| n-C₄H₉–* | D4-10 |
| cyclohexyl–* | D4-11 |
| 4-EtO-C₆H₄–* | D4-12 |
| 4-(PhNHC(O))C₆H₄–* | D4-13 |
| 4-(MeNHC(O))C₆H₄–* | D4-14 |
| 4-(MeO₂C)C₆H₄–* | D4-15 |
| 4-Cl-C₆H₄–* | D4-16 |

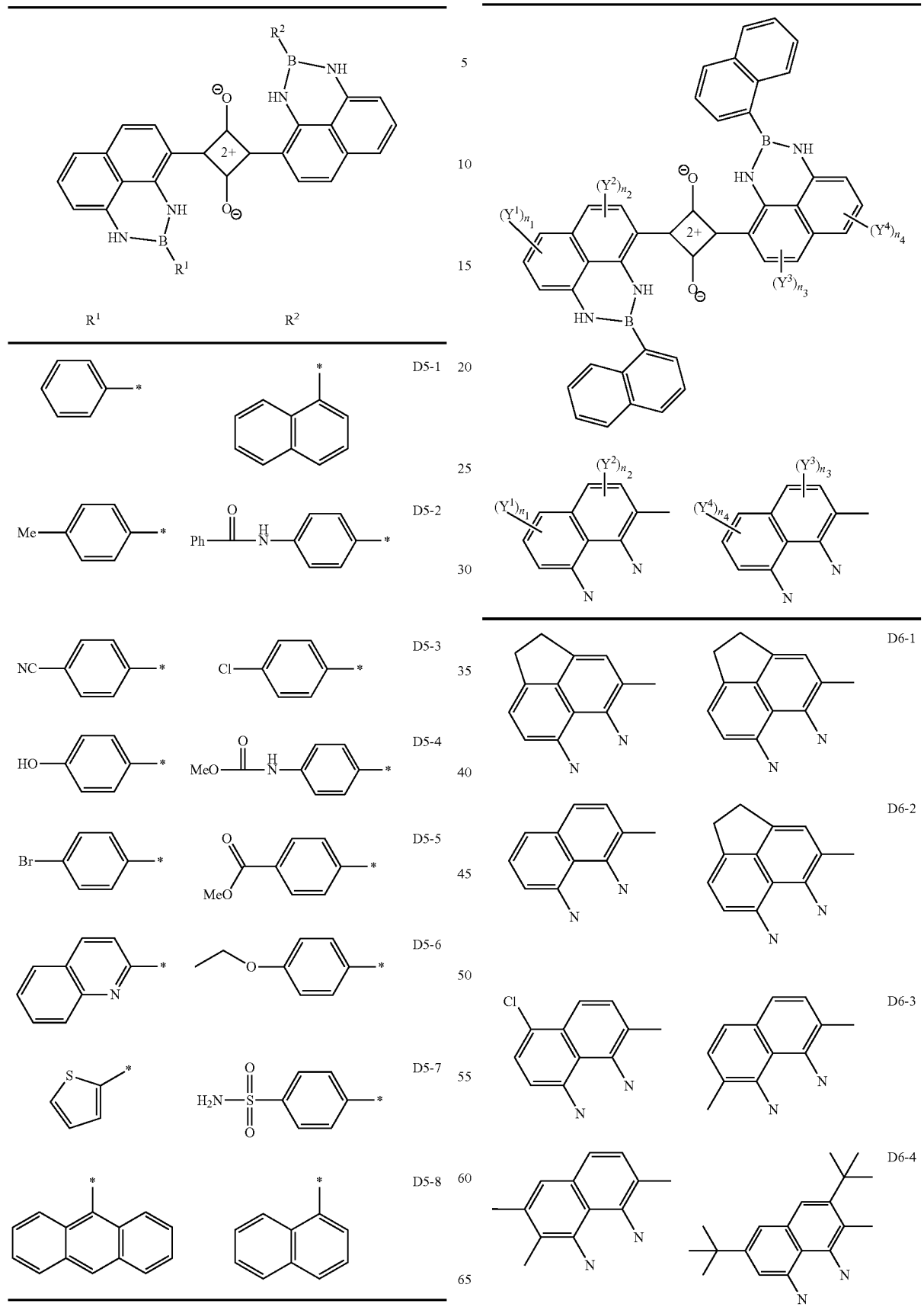

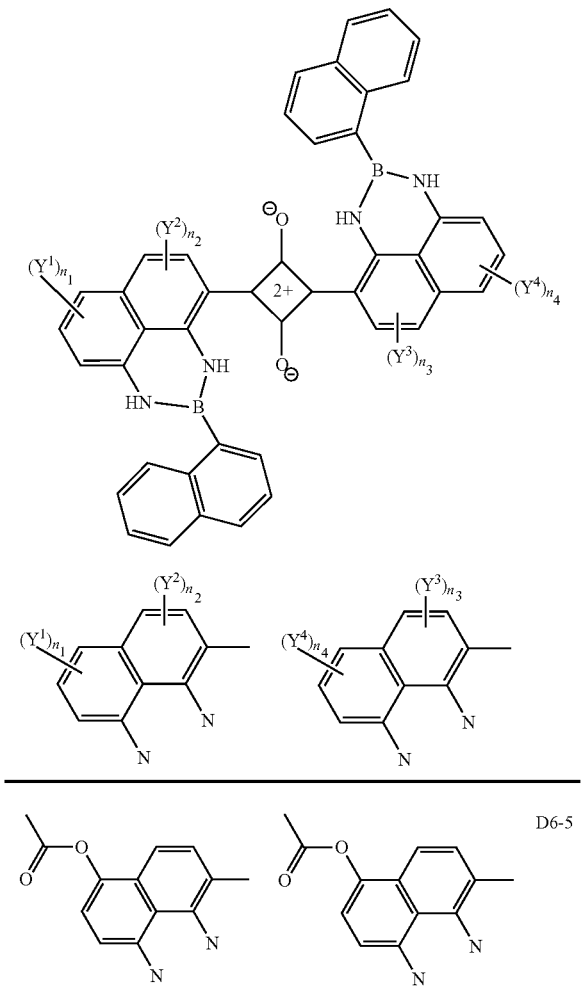

The squarylium compound of the present invention has a maximum peak in an infrared ray region, and is commonly in a range of from 700 nm to 1200 nm, and preferably from 750 nm to 1000 nm. In the invention, the maximum peak may be measured by dissolving a squarylium compound in a suitable solvent (for example, tetrahydrofuran, N,N-dimethylacetamide or the like) and measuring a spectrum in a wavelength range of 350 nm to 1200 nm using UV3100 (trade name, UV/VIS spectrophotometer manufactured by Shimadzu Corporation). In addition, a molar absorption coefficient of the squarylium compound is not limited, but is preferably from 25,000 to 250,000, more preferably 50,000 to 200,000.

The squarylium compound of the present invention is invisible, and it is thus preferably transparent. However, the compound may exhibit a faint color such as green, gray or brown.

2. Composition

The composition containing the squarylium compound of the present invention may be aqueous or non-aqueous.

For the aqueous composition, for example, a mixture containing at least water as a main component and optionally containing a hydrophilic organic solvent may be used. Examples of the hydrophilic organic solvent include: alcohols such as methanol, ethanol, propanol, isopropanol, butanol, isobutanol, sec-butanol, t-butanol, pentanol, hexanol, cyclohexanol, or benzyl alcohol; polyhydric alcohols such as ethylene glycol, diethylene glycol, triethylene glycol, polyethylene glycol, propylene glycol, dipropylene glycol, polypropylene glycol, butylene glycol, hexanediol, pentanediol, glycerin, hexanetriol or thiodiglycol; glycol derivatives such as ethylene glycol monomethyl ether, ethylene glycol monoethyl ether, ethylene glycol monobutyl ether, diethylene glycol monomethyl ether, diethylene glycol monobutyl ether, propylene glycol monomethyl ether, propylene glycol monobutyl ether, dipropylene glycol monomethyl ether, triethylene glycol monomethyl ether, ethylene glycol diacetate, ethylene glycol monomethyl ether acetate, triethylene glycol monoethyl ether, or ethylene glycol monophenyl ether; amines such as ethanolamine, diethanolamine, triethanolamine, N-methyldiethanolamine, N-ethyldiethanolamine, morpholine, N-ethylmorpholine, ethylenediamine, diethylenetriamine, triethylenetetramine, polyethyleneimine, or tetramethylpropylenediamine; amides such as formamide, N,N-dimethylformamide, or N,N-dimethylacetamide; and other solvents such as dimethylsulfoxide, sulfolane, 2-pyrrolidone, N-methyl-2-pyrrolidone, N-vinyl-2-pyrrolidone, 2-oxazolidone, 1,3-dimethyl-2-imidazolidinone, acetonitrile, or acetone.

The aqueous composition in the present invention may further contain an aqueous resin. Examples of the aqueous resin include a water-soluble resin, a water-dispersible resin and a mixture thereof. Specific examples of the aqueous resin include acrylic resins, styrene-acrylic resins, polyester resins, polyamide resins, polyurethane resins and fluorine-containing resins.

The content of water as a solvent of the aqueous composition is preferably from 30% to 100% by volume, and more preferably from 50% to 100% by volume, with respect to the aqueous composition.

The aqueous composition in the invention may further contain a surfactant and/or a dispersant. Examples of the surfactant include anionic, nonionic, cationic and amphoteric surfactants and any of these surfactants may be used.

Examples of anionic surfactants include fatty acid salts, alkylsulfuric acid ester salts, alkylbenzenesulfonates, alkylnaphthalenesulfonates, dialkylsulfosuccinates, alkyldiaryl ether disulfonates, alkylphosphates, polyoxyethylene alkyl ether sulfates, polyoxyethylene alkylaryl ether sulfates, naphthalenesulfonic acid-formalin condensate, polyoxyethylene alkylphosphoric acid ester salts, glycerol borate fatty acid ester, and polyoxyethylene glycerol fatty acid ester.

Examples of nonionic surfactants include polyoxyethylene alkyl ethers, polyoxyethylene alkylaryl ethers, polyoxyethylene oxypropylene block copolymers, sorbitan fatty acid ester, polyoxyethylenesorbitan fatty acid ester, polyoxyethylene sorbitol fatty acid ester, glycerin fatty acid ester, polyoxyethylene fatty acid ester, polyoxyethylenealkylamine, fluorine-containing surfactants, and silicon surfactants.

Examples of cationic surfactant include alkylamine salts and tertiary ammonium salts.

Examples of amphoteric surfactants include alkyl betaine and amine oxide.

An example of the non-aqueous composition may be a composition obtained by dispersing the squarylium compound of the invention in a non-aqueous vehicle.

Examples of resins used for non-aqueous vehicles include petroleum resins, casein, shellac, rosin-modified maleic acid resins, rosin-modified phenol resins, nitrocellulose, cellulose acetatebutylate, cyclized rubbers, chlorinated rubbers, oxidized rubbers, hydrochlorinated rubbers, phenol resins, alkyd resins, polyester resins, unsaturated polyester resins, amino resins, epoxy resins, vinyl resins, vinyl chloride, vinyl chloride-vinyl acetate copolymers, acrylic resins, methacrylic resins, polyurethane resins, silicon resins, fluororesins, drying oils, synthetic drying oils, styrene/maleic acid resins, styrene/acrylic resins, polyamide resins, polyimide resins, polyester resins, benzoguanamine resins, melamine resins, urea resin, chlorinated polypropylene, butyral resins and vinylidene chloride resins. As the non-aqueous vehicle, a photo-curable resin or a thermosetting resin may be used.

Examples of solvents used for non-aqueous vehicles include aromatic solvents such as toluene, xylene or methoxy benzene; ester acetate solvents such as ethyl acetate, butyl acetate, propylene glycol monomethyl ether acetate or propylene glycol monoethyl ether acetate; propionate solvents such as ethoxyethylpropionate; alcohol solvents such as methanol or ethanol; ether solvents such as butyl cellosolve, propylene glycol monomethyl ether, diethyleneglycol ethyl ether, or diethylene glycol dimethyl ether; ketone solvents such as methyl ethyl ketone, methyl isobutyl ketone or cyclohexanone; aliphatic hydrocarbon solvents such as hexane; nitrogen compound solvents such as N,N-dimethylformamide, γ-butyrolactam, N-methyl-2-pyrrolidone, aniline or pyridine; lactone solvents such as γ-butyrolactone; and ester carbamates such as a 48:52 mixture of methyl carbamate and ethyl carbamate.

When the squarylium compound of the present invention is in a form of microparticles, for example, the volume average microparticle diameter of microparticles is preferably from 1 nm to 1,000 nm, particularly preferably from 10 nm to 500 nm. Herein, the volume average microparticle diameter of microparticles refers to an average diameter of microparticles theirselves, or when an additive such as a dispersant is adhered to the microparticles, the volume average microparticle diameter of microparticles refers to an average diameter of the microparticles having thereon the additive. In the present invention, the volume average microparticle diameter of microparticles may be measured using a NANOTRAC UPA microparticle size analyzer (trade name: UPA-EX150, manufactured by NIKKISO CO., LTD.). The measurement is carried out by a predetermined measurement method using 3 mL of a microparticle dispersant put into a measuring cell. In addition, for parameters input during measurement, an ink viscosity and a microparticle density are used as a viscosity and a density of dispersed microparticles, respectively.

The concentration of the squarylium compound contained in the composition of the present invention is preferably from 0.1% by mass to 35% by mass, and more preferably from 0.5% by mass to 25% by mass, with respect to the total amount of the composition.

The composition of the present invention may further contain a variety of additives according to purposes and applications. Examples of additives include surface tension adjusters, viscosity adjusters, specific resistance adjusters, anti-foaming agents and preservatives.

When the composition of the present invention is used as a coating composition, the composition may be applied by a known coating method. For example, the coating may be carried out by a known coating method using a bar coater, an extrusion die coater, an air doctor coater, a blade coater, a rod coater, a knife coater, a squeeze coater, a reverse roll coater or the like.

For example, when the composition of the invention is used to obtain an optical film, the coating composition of the invention is applied on a transparent substrate as a substrate to be coated, to form a layer containing the squarylium compound of the invention. The material of the transparent substrate may be not limited, as long as it is substantially transparent. Examples of materials of the substrate include glasses, polyester resins, polyolefin resins, polycarbonate resins, poly(meth)acrylic acid ester resins, polystyrene resins, polyvinyl chloride resins, polyvinyl acetate resins, polyarylate resins and polyether sulfone resins.

The squarylium compound, and the composition and infrared absorbent (described below) of the present invention may be used for various applications. Examples thereof include image recording materials for forming images, in particular, invisible images. Specifically, preferred examples include ink jet recording materials, printing inks (such as security ink or invisible bar code ink), recording pens, thermosensitive recording materials, pressure-sensitive recording materials, electrophotographic recording materials, and transcription-type halogenated silver photosensitive materials. In addition, the squarylium compound, the composition and infrared absorbent of the present invention may be applied to optical films such as infrared ray cut films or heat ray shielding films for solid-state image sensing devices (such as a CCD) or displays (such as a plasma display). Further, the squarylium compound, the composition and infrared absorbent of the present invention may be applied to recordable optical discs or photothermal conversion materials for flash welding and dying liquids for dying a variety of fabrics. In addition, the squarylium compound, the composition and infrared absorbent of the present invention may be applied to markers for diagnosis, photodynamic therapy and the like due to absorbability in an infrared region exhibiting superior human permeability.

3. Infrared Absorbent

The infrared absorbent of the present invention contains at least a compound represented by the following Formula (1A) or a composition containing the same.

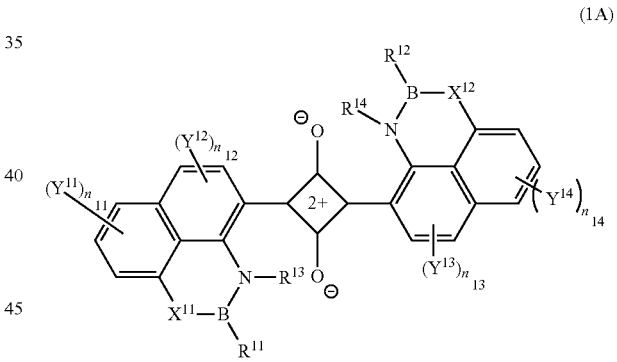

(1A)

In Formula (1A), $R^{11}$ and $R^{12}$ each independently represent a substituted or unsubstituted alkyl group, a substituted or unsubstituted cycloalkyl group, a substituted or unsubstituted aryl group, or a substituted or unsubstituted heteroaryl group;

$R^{13}$ and $R^{14}$ each independently represent a hydrogen atom, or a substituted or unsubstituted alkyl group;

$X^{11}$ and $X^{12}$ each independently represent an oxygen atom or —$NR^{15}$—, in which $R^{15}$ represents a hydrogen atom or a substituted or unsubstituted alkyl group;

$Y^{11}$, $Y^{12}$, $Y^{13}$ and $Y^{14}$ each independently represent a halogen atom, a substituted or unsubstituted alkyl group, a substituted or unsubstituted cycloalkyl group, a substituted or unsubstituted aryl group, a substituted or unsubstituted heteroaryl group, a substituted or unsubstituted arylcarbonyloxy group, or a substituted or unsubstituted alkylcarbonyloxy group;

when there are plural $Y^{11}$'s, the plural $Y^{11}$'s may be bonded to each other to form a ring structure; when there are plural $Y^{12}$'s, the plural $Y^{12}$'s may be bonded to each other to form a ring structure; when there are plural $Y^{13}$'s, the plural $Y^{13}$'s may be bonded to each other to form a ring structure; when there are plural $Y^{14}$'s, the plural $Y^{14}$'s may be bonded to each other to form a ring structure;

$Y^{11}$ and $Y^{12}$ may be bonded together to form a ring structure; and $Y^{13}$ and $Y^{14}$ may be bonded together to form a ring structure;

$n_{11}$ and $n_{14}$ each independently represent an integer of from 6 to 3; and $n_{12}$ and $n_{13}$ each independently represent an integer of from 0 to 2.

In Formula (1A), $R^{11}$ represents an alkyl group, a cycloalkyl group, an aryl group, or a heteroaryl group. The carbon number and constituent atom number of these groups are not limited, and these groups preferably have the same definitions (including preferred examples) as those described for $R^1$.

These groups may each have a substituent and may not have a substituent. Examples of the substituent which may be held by the groups (hereinafter, a substituent group exemplified below may be referred to as "a substituent S") include: alkyl groups (preferably having 1 to 30 carbon atoms, more preferably having 1 to 20 carbon atoms, and particularly preferably having 1 to 8 carbon atoms) such as a methyl group, an ethyl group, an iso-propyl group, a tert-butyl group, a n-octyl group, a n-decyl group, a n-hexadecyl group, a cyclopropyl group, a cyclopentyl group or a cyclohexyl group; alkenyl groups (preferably having 2 to 30 carbon atoms, more preferably having 2 to 20 carbon atoms, and particularly preferably having 2 to 10 carbon atoms) such as a vinyl group, an allyl group, a 2-butenyl group or a 3-pentenyl group; alkynyl groups (preferably having 2 to 30 carbon atoms, more preferably having 2 to 20 carbon atoms, and particularly preferably having 2 to 10 carbon atoms) such as a propargyl group or a 3-pentynyl group; aryl groups (preferably having 6 to 30 carbon atoms, more preferably having 6 to 20 carbon atoms, and particularly preferably having 6 to 12 carbon atoms) such as a phenyl group, a p-methylphenyl group, a biphenyl group, a naphthyl group, an anthranyl group, or a phenanthryl group; amino groups (preferably having 0 to 30 carbon atoms, more preferably having 0 to 20 carbon atoms, and particularly preferably having 0 to 10 carbon atoms) such as an alkylamino group, an arylamino group, or a heterocyclic amino group, specific examples thereof including an amino group, a methylamino group, a dimethylamino group, a diethylamino group, a dibenzylamino group, a diphenylamino group, or a dioctylamino group; alkoxy groups (preferably having 1 to 30 carbon atoms, more preferably having 1 to 20 carbon atoms, and particularly preferably having 1 to 8 carbon atoms) such as a methoxy group, an ethoxy group, a butoxy group, or a 2-ethylhexyloxy group; aryloxy groups (preferably having 6 to 30 carbon atoms, more preferably having 6 to 20 carbon atoms, and particularly preferably having 6 to 12 carbon atoms) such as a phenyloxy group, a 1-naphthyloxy group, or a 2-naphthyloxy group; aromatic heterocyclooxy groups (preferably having 1 to 30 carbon atoms, more preferably having 1 to 20 carbon atoms, and particularly preferably having 1 to 12 carbon atoms) such as a pyridyloxy group, a pyrazyloxy group, a pyrimidyloxy group, or a quinolyloxy group;

alkylcarbonyl or arylcarbonyl groups (preferably having 2 to 30 carbon atoms, more preferably having 2 to 20 carbon atoms, and particularly preferably having 2 to 12 carbon atoms) such as an acetyl group, a benzoyl group, a formyl group, or a pivaloyl group;

alkyloxycarbonyl groups (preferably having 2 to 30 carbon atoms, more preferably having 2 to 20 carbon atoms, and particularly preferably having 2 to 7 carbon atoms) such as a methoxycarbonyl group or an ethoxycarbonyl group;

alkylcarbonyloxy groups (preferably having 2 to 30 carbon atoms, more preferably having 2 to 20 carbon atoms, and particularly preferably having 2 to 7 carbon atoms) such as a methylcarbonyloxy group or an ethylcarbonyloxy group; aryloxycarbonyl groups (preferably having 7 to 30 carbon atoms, more preferably having 7 to 20 carbon atoms, and particularly preferably having 7 to 11 carbon atoms) such as a phenyloxycarbonyl group; arylcarbonyloxy groups (preferably having 7 to 30 carbon atoms, more preferably having 7 to 20 carbon atoms, particularly preferably having 7 to 11 carbon atoms) such as a phenylcarbonyloxy group; alkylcarbonylamino or arylcarbonylamino groups (preferably having 2 to 30 carbon atoms, more preferably having 2 to 20 carbon atoms, and particularly preferably having 2 to 12 carbon atoms) such as an acetylamino group or a benzoylamino group; alkyloxycarbonylamino groups (preferably having 2 to 30 carbon atoms, more preferably having 2 to 20 carbon atoms, and particularly preferably having 2 to 12 carbon atoms) such as a methoxycarbonylamino group; aryloxycarbonylamino groups (preferably having 7 to 30 carbon atoms, more preferably having 7 to 20 carbon atoms, and particularly preferably having 7 to 12 carbon atoms) such as a phenyloxycarbonylamino group; sulfonylamino groups (preferably having 1 to 30 carbon atoms, more preferably having 1 to 20 carbon atoms, and particularly preferably having 1 to 12 carbon atoms) such as a methanesulfonylamino group or a benzenesulfonylamino group; sulfamoyl groups (preferably having 0 to 30 carbon atoms, more preferably having 0 to 20 carbon atoms, and particularly preferably having 0 to 12 carbon atoms) such as a sulfamoyl group, a methylsulfamoyl group, a dimethylsulfamoyl group, or a phenylsulfamoyl group; carbamoyl groups, alkylcarbamoyl groups (preferably having 2 to 30 carbon atoms, more preferably having 2 to 20 carbon atoms, and particularly preferably having 2 to 7 carbon atoms) such as a methylcarbamoyl group or a diethylcarbamoyl group; arylcarbamoyl groups (preferably having 7 to 30 carbon atoms, more preferably having 7 to 20 carbon atoms, and particularly preferably having 7 to 11 carbon atoms) such as a phenylcarbamoyl group; alkylaminocarbonyl amino or arylaminocarbonyl amino groups (preferably having 2 to 30 carbon atoms, more preferably having 2 to 20 carbon atoms, and particularly preferably having 2 to 12 carbon atoms) such as a dimethylamino carbonylamino group or an anilinocarbonylamino group; alkylthio groups (preferably having 1 to 30 carbon atoms, more preferably having 1 to 20 carbon atoms, and particularly preferably having 1 to 12 carbon atoms) such as a methylthio group or an ethylthio group; arylthio groups (preferably having 6 to 30 carbon atoms, more preferably having 6 to 20 carbon atoms, and particularly preferably having 6 to 12 carbon atoms) such as a phenylthio group;

aromatic heterocyclicthio groups (preferably having 1 to 30 carbon atoms, more preferably having 1 to 20 carbon atoms, and particularly preferably having 1 to 12 carbon atoms) such as a pyridylthio group, a 2-benzimidazolylthio group, a 2-benzoxazolylthio group, or a 2-benzothiazolylthio group; sulfonyl groups (preferably having 1 to 30 carbon atoms, more preferably having 1 to 20 carbon atoms, and particularly preferably having 1 to 12 carbon atoms) such as a mesyl group, or a tosyl group; sulfonyl groups (preferably having 1 to 30 carbon atoms, more preferably having 1 to 20 carbon atoms, and particularly preferably having 1 to 12 carbon atoms) such as a methanesulfinyl group, or a benzenesulfinyl group; ureido groups (preferably having 1 to 30 carbon atoms, more preferably having 1 to 20 carbon atoms, and particularly preferably having 1 to 12 carbon atoms) such as a ureido group, a methylureide group, or a phenylureido group; amide phosphate groups (preferably having 1 to 30 carbon atoms, more preferably having 1 to 20 carbon atoms, and particularly preferably having 1 to 12 carbon atoms) such as a diethylamide phosphate group, or a phenylamide phosphate group; a hydroxyl group; a mercapto group; a halogen atom (for example, a fluorine atom, a chlorine atom, a bromine atom, an iodine atom); a cyano group; a sulfo group; a carboxyl group; a nitro group; a hydroxamic group; a sulfino group; a hydrazino group; an imino group; a heterocyclic group (preferably having 1 to 30 carbon atoms, and more preferably having 1 to 12 carbon atoms) containing, as a heteroatom, a nitrogen atom, an oxygen atom, a sulfur atom, or the like, such as an imidazolyl group, a pyridyl group, a quinolyl group, a furyl group, a thienyl group, a piperidyl group, a morpholino group, a benzoxazolyl group, a benzoimidazolyl group, a benzothiazolyl group, a carbazolyl group, or an azepinyl group; and silyl groups (preferably having 3 to 40 carbon atoms, more preferably having 3 to 30 carbon atoms, and particularly preferably having 3 to 24 carbon atoms) such as a trimethylsilyl group or a triphenylsilyl group. In addition, for the substituent mentioned in the present specification, for example in the case of the expression "alkyloxycarbonyl group having 2 to 30 carbon atoms", the number of carbon atoms includes the carbon number of the alkyl group and the carbon number of the carbonyl group. That is, the alkyloxycarbonyl group having 2 carbon atoms refers to a methyloxycarbonyl group. Similarly, in the case where a carbamoyl group is contained in the substituent, the carbon number of the substituent includes the carbon number of carbamoyl group.

Examples of preferred substituents S include an alkyl group, an alkoxy group, a hydroxyl group, a carboxyl group, a carbamoyl group, a halogen atom, a nitro group, a cyano group, a mercapto group, an alkylcarbonyl group, an arylcarbonyl group, an alkyloxycarbonyl group, an aryloxycarbonyl group, an alkylcarbonyloxy group, an arylcarbonyloxy group, an alkylcarbonylamino group, an arylcarbonylamino group, an alkyloxycarbonylamino group, an aryloxycarbonylamino group, an alkylcarbamoyl group and an arylcarbamoyl group.

In particular, more preferred substituents S are an alkyl group having 1 to 8 carbon atoms, an alkoxy group having 1 to 8 carbon atoms, a hydroxyl group, a carboxyl group, a carbamoyl group, a halogen atom, an alkyloxycarbonyl group having 2 to 7 carbon atoms, an aryloxycarbonyl group having 7 to 11 carbon atoms, an alkylcarbonyloxy group having 2 to 7 carbon atoms, an arylcarbonyloxy group having 7 to 11 carbon atoms, an alkylcarbamoyl group having 2 to 7 carbon atoms, an arylcarbamoyl group having 7 to 11 carbon atoms and the like. Even more preferred substituents S are an alkyl group having 1 to 4 carbon atoms, an alkoxy group having 1 to 4 carbon atoms, a hydroxyl group, a carboxyl group, a carbamoyl group and a halogen atom.

$R^{12}$ represents an alkyl group, a cycloalkyl group, an aryl group, a heteroaryl group or the like. These groups may each have a substituent and may not have a substituent. The alkyl group, cycloalkyl group, aryl group, heteroaryl group and substituents thereof have the same definitions (including preferred examples) as those described for $R^1$.

In the present invention, $R^{11}$ and $R^{12}$ preferably represent the same group.

$R^{13}$ represents a hydrogen atom, or a substituted or unsubstituted alkyl group. The carbon number of the alkyl group represented by $R^{13}$ is not limited, and the alkyl group has the same definition (including preferred examples) as that described for $R^3$. The substituent has the same definition (including preferred examples) as the substituent S described above.

$R^{14}$ represents a hydrogen atom, or a substituted or unsubstituted alkyl group. The carbon number of the alkyl group represented by $R^{14}$ is not limited, and the alkyl group has the same definition (including preferred examples) as that described for $R^3$. The substituent has the same definition (including preferred examples) as the substituent S described above.

In the present invention, $R^{13}$ and $R^{14}$ preferably represent the same group.

$X^{11}$ and $X^{12}$ independently represent an oxygen atom (—O—) or —$NR^{15}$—, in which $R^{15}$ represents a hydrogen atom or a substituted or unsubstituted alkyl group. The carbon number of the alkyl group represented by $R^{15}$ is not limited, and the alkyl group represented by $R^{15}$ has the same definition (including preferred examples) as that described for $R^3$. The substituent has the same definition (including preferred examples) as the substituent S described above. $X^{11}$ is preferably $X^1$, and $X^{12}$ is preferably $X^2$.

In the present invention, $X^{11}$ and $X^{12}$ preferably represent the same group.

$Y^{11}$ represents a halogen atom, a substituted or unsubstituted alkyl group, a substituted or unsubstituted cycloalkyl group, a substituted or unsubstituted aryl group, a substituted or unsubstituted heteroaryl group, a substituted or unsubstituted arylcarbonyloxy group, or a substituted or unsubstituted alkylcarbonyloxy group. The carbon number and constituent atom number of these groups are not limited, and these groups have the same definitions (including preferred examples) as those described for $Y^1$.

When the group represented by $Y^{11}$ has a substituent, the substituent has the same definition (including preferred examples) as the substituent S described above. Among preferred embodiments, most preferred substituents include a halogen atom, an alkyl group having 1 to 6 carbon atoms, and an alkoxy group having 1 to 6 carbon atoms.

When there are plural $Y^{11}$'s, $Y^{12}$'s, $Y^{13}$'s, or $Y^{14}$'s, they may be bonded together to form a ring structure, respectively. For example, when plural $Y^{11}$'s are present, the plural $Y^{11}$'s may be bonded to each other and form, for example, a tricyclic ring such as anthracene ring together with the naphthalene ring to which $Y^{11}$ and $Y^{12}$ are directly bonded. Alternatively, $Y^{11}$ and $Y^{12}$ may be bonded to each other and form, for example, a tricyclic ring such as an acenaphthene ring or an acenaphthylene ring together with the naphthalene to which $Y^{11}$ and $Y^{12}$ are directly bonded.

In Formula (1A), $n_{11}$ and $n_{14}$ each represent an integer of from 0 to 3, preferably an integer of from 0 to 1, and particularly preferably 0. Furthermore, $n_{12}$ and $n_{13}$ each represent an integer of from 0 to 2, preferably an integer of from 0 to 1, and particularly preferably 0.

The squarylium compound contained in the infrared absorbent of the present invention is preferably represented by Formula (1) described above, more preferably represented by Formula (1a), and most preferably represented by Formula (1b).

Since the infrared absorbent of the invention has the following structure in which a boron atom is introduced into a conventional squarylium compound, an absorption peak region thereof is in a relatively longer wavelength, while high robustness and invisibility are maintained. It is reasoned that formation of a boron complex causes improvement in planarity of molecules, widens the conjugated plane, and attracts electrons covalently bonded to boron atoms to atoms with high electronegativity, to realize long wavelength and high robustness.

Accordingly, any technical concept falls within the scope of the present invention so long as the following structure and effects of the present invention (for example, presence of wavelengths of maximum peaks in an infrared absorption region) are obtained. For example, complexes of the squarylium of the present invention and a metal, derivatives in which the squarylium compound of the present invention is introduced into another compound, and polymers of the squarylium compound of the present invention fall within the scope of the technical concept of the present invention.

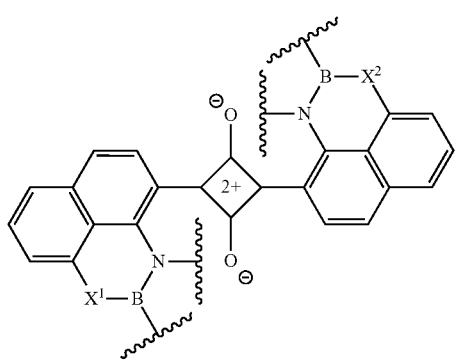

4. Production Method

A method for producing an infrared absorbent represented by Formula (1) of the invention includes: reacting a compound (2) represented by the following Formula (2) and a compound (3) represented by the following Formula (3) with squaric acid (specifically, a compound represented by the following Formula (4)).

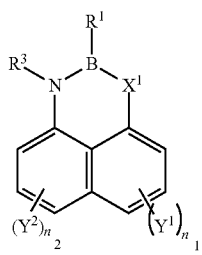
(2)

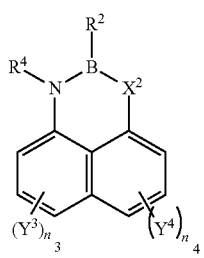
(3)

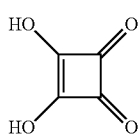
(4)

The solvent used for the production method of the present invention is preferably selected from solvents which are capable of dissolving the compound (2), the compound (3) and squaric acid and exhibiting low solubility to the target product, i.e., the compound (1). An example of such a solvent is a solvent containing at least an alcohol. The alcohol is preferably an alkyl alcohol having 1 to 5 carbon atoms, particularly preferably an alkyl alcohol having 3 to 4 carbon atoms, and most preferably butanol.

Preferably, the solvent further contains an aromatic solvent. When the solvent further contains an aromatic solvent, solubility of the compound (2) and the compound (3) is improved, and solubility of the reaction system is arbitrary controlled. Any aromatic solvent may used so long as it has an aromatic ring, and examples of preferred aromatic solvents include toluene, xylene, mesitylene, chlorobenzene, dichlorobenzene, and an alkyl group-substituted benzene or a halogen-substituted benzene such as cymene.

For example, when a mixed liquid of an alcohol solvent and an aromatic solvent is used, the preferred mixing ratio thereof (i.e., alcohol solvent:aromatic solvent) is from 90:10 to 10:90 (v/v), and more preferably from 80:20 to 20:80 (v/v).

The reaction is carried out preferably, for example, at a temperature of 50 to 140° C., particularly preferably at 70 to 120° C.

The reaction may be carried out under an air atmosphere or under an inert gas such as nitrogen.

The reaction may be carried out under a reduced pressure or an atmospheric pressure.

The reaction period may be suitably determined according to the type of raw materials, solvent, reaction temperature or the like, and is commonly from about 30 minutes to 6 hours, and preferably from 1 hour to 4 hours.

The amounts of compound (2), compound (3) and squaric acid to be added is, for example, as follows: that is, the amount of compound (2) is commonly from 0.5 moles to 5.0 moles (preferably 0.8 moles to 2 moles), and the amount of compound (3) is commonly from 0.5 moles to 5 moles (preferably 0.8 moles to 2 moles), with respect to 1 mole of squaric acid.

When the compound (2) is used instead of the compound (3), that is, in the case where only the compound (2) and squaric acid are allowed to react, the amount of compound (2) is commonly from 1 mole to 10 moles, preferably from 1.6 moles to 4 moles, with respect to 1 mole of squaric acid.

In the production method, stirring may be optionally performed, and a post-treatment process such as filtration, washing, or recrystallization may be further performed.

Pre-Process

The production method may further include a preparation process of the compound (2).

The process for preparing the compound (2) is preferably reacting a boronic acid compound represented by the following Formula (5) with a 1,8-diaminonaphthalene compound or 1-amino-8-hydroxynaphthalene compound:

(5)

wherein, in Formula (5), $R^1$ has the same definition as that in Formula (1); R's independently represents a hydrogen atom or an alkyl group having 1 to 3 carbon atoms, and R's may be bonded to each other.

R's are not particularly limited as long as a complex forming reaction proceeds. Examples of preferred R's include a hydrogen atom, and alkyl groups having 1 to 3 carbon atoms. R's may be combined with each other. When R's are bonded with each other, R's may form a 5- to 9-membered ring (preferably a 5- to 7-membered ring) including boron and oxygen atoms, of which the ring may be substituted by one or more substituents such as a methyl group or an ethyl group.

The compound represented by Formula (5) preferably has a structure in which R's represent a hydrogen atom, or a structure represented by the following formula:

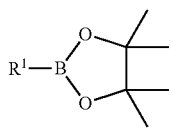

As used herein, the "1,8-diaminonaphthalene compound" refers to 1,8-diaminonaphthalene and a derivative thereof, and is specifically represented by the following Formula (6):

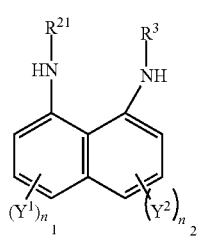

(6)

wherein, in Formula (6), $R^{21}$ has the same definition (including preferred examples) as that described for $R^3$ in Formula (2), and $R^3$, $Y^1$, $Y^2$, $n_1$, and $n_2$ have the same definitions as those of Formula (2), respectively.

As used herein, the "1-amino-8-hydroxynaphthalene compound" refers to 1-amino-8-hydroxynaphthalene and a derivative thereof, and is specifically represented by the following Formula (7):

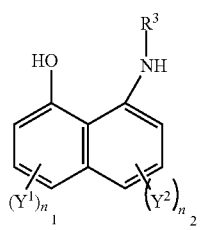

(7)

wherein, in Formula (7), $R^3$, $Y^1$, $Y^2$, $n_1$, and $n_2$ have the same definitions as those of Formula (2), respectively.

In the pre-process, for example, the compound (2) may be suitably obtained by refluxing raw materials under heating in a solvent.

The solvent used for the pre-process is not particularly limited so long as it is capable of dissolving raw materials, but is, for example, preferably, an alcohol solvent. For example, the alcohol solvent is preferably an alkyl alcohol having 1 to 4 carbon atoms, and more preferably an alkyl alcohol having 1 to 3 carbon atoms. Specific examples of the alcohol solvent include methanol, ethanol, and 2-propanol.

An acid catalyst may be optionally used. As a result, it is advantageous since the reaction period shortens. Examples of useful acid catalysts include sulfuric acid, p-toluenesulfonic acid and polyphosphoric acid.

The reaction is carried out preferably, for example, at a temperature of 30 to 90° C., and particularly preferably, at 40 to 80° C.

The reaction may be carried out under an air atmosphere or under an inert gas such as nitrogen.

The reaction may be carried out under a reduced pressure or an atmospheric pressure.

The reaction period (in particular, reflux period) may be suitably determined according to the type of raw materials, solvent, reaction temperature or the like, and is commonly from about 30 minutes to 6 hours, preferably from about 1 hour to 4 hours.

The mixing ratio of the boronic acid compound and the 1,8-diaminonaphthalene compound or 1-amino-8-hydroxynaphthalene compound is, for example, as follows: that is, the amount of 1,8-diaminonaphthalene compound or 1-amino-8-hydroxynaphthalene compound is from 0.2 moles to 5 moles (preferably, 0.5 moles to 2 moles) with respect to 1 mole of the boronic acid compound.

In the pre-process, stirring may be optionally performed, and a post-treatment such as filtration, washing, or recrystallization may be further performed.

The compound (3) may be produced in the same manner as in the production of compound (2) except that the following compound is used as a raw material.

(5')

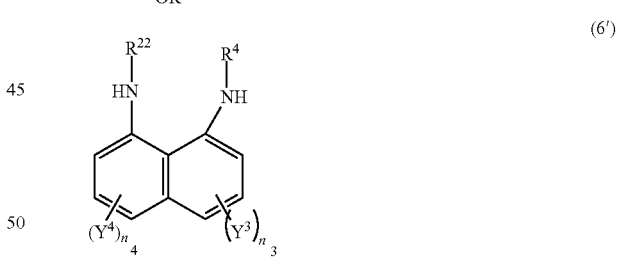

(6')

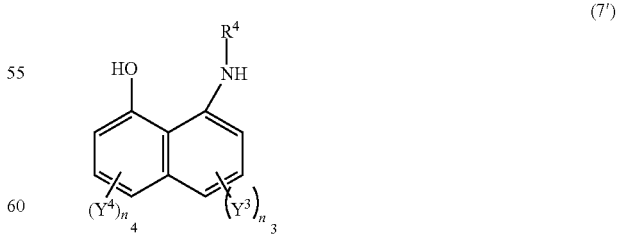

(7')

In Formulae (5'), (6'), and (7'), $R^2$, $R^4$, $Y^3$, $Y^4$, $n_3$, $n_4$ in Formulae (5'), (6') and (7') have the same definitions as those in Formula (3), respectively; and $R^{22}$ has the same definition (including preferred examples) as that described for $R^4$.

EXAMPLES

The present invention will be described in more detail with reference to the following examples, but is not limited thereto.

Example 1

Synthesis of Compound D1-7

A compound D1-7 was synthesized in accordance with the following scheme.

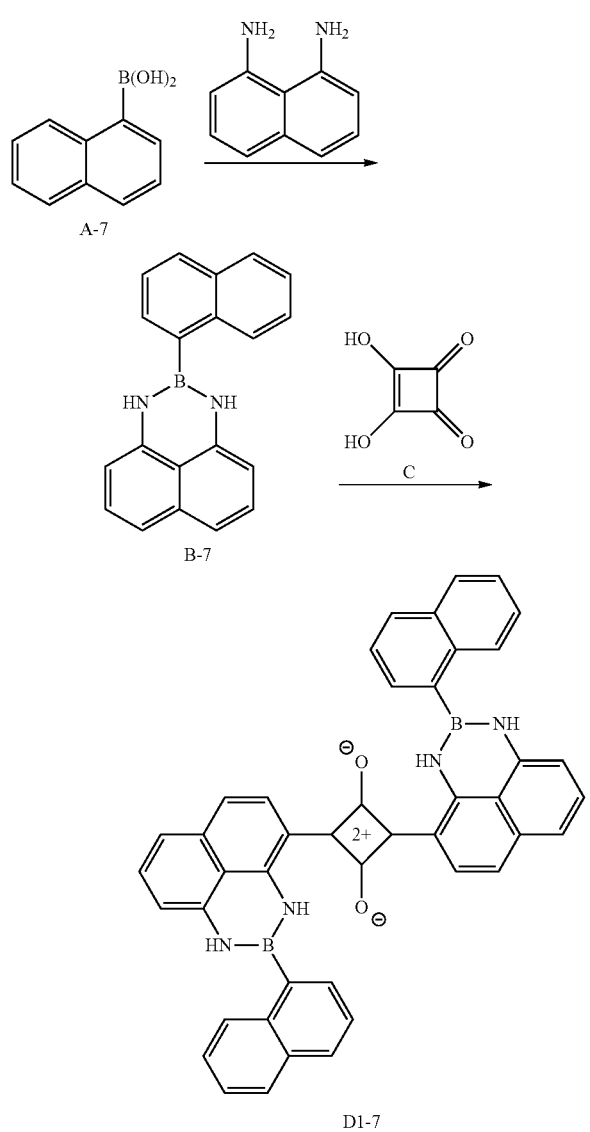

A compound A-7 (7.8 g), 1,8-diaminonaphthalene (7.2 g) and p-toluenesulfonic acid monohydrate (0.3 g) were refluxed under heating in methanol (45 mL) for 3 hours. The reaction liquid was cooled to ambient temperature, and the resulting crystal was filtered, thereby obtaining a compound B-7 (11.7 g, yield: 66%).

The compound B-7 (9.8 g) and toluene (75 mL) were added to the compound C (1.9 g) and n-butanol (25 mL), followed by refluxing with heating for 3 hours. The reaction liquid was cooled to ambient temperature, and the resulting crystal was filtered. The obtained solid was refluxed with heating in tetrahydrofuran (50 mL) for 30 minutes, and cooled to ambient temperature, and the resulting crystal was filtered, thereby obtaining a compound D1-7 (7.2 g, yield: 65%).

MALDI-TOF-MASS:

calcd. for C44H28B2N4O2[M+H]+666.24,

FOUND; 666.12

Example 2

Synthesis of Compound D1-1

A compound D1-1 was obtained in the same manner as in Example 1 except that compound A-1 was used instead of compound A-7.

MALDI-TOF-MASS:

calcd. for C36H24B2N4O2[M+H]+566.22,

FOUND; 566.06

Example 3

Synthesis of Compound D1-2

A compound D1-2 was obtained in the same manner as in Example 1 except that compound A-2 was used instead of compound A-7.

MALDI-TOF-MASS:

calcd. for C38H28B2N4O2[M+H]+594.24,

FOUND; 593.81

Example 4

Synthesis of Compound D1-3

A compound D1-3 was obtained in the same manner as in Example 1 except that compound A-3 was used instead of compound A-7.

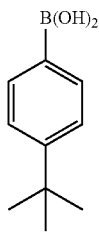

A-3

MALDI-TOF-MASS:
calcd. for C44H40B2N4O2[M+H]+678.33,
FOUND; 678.14

Example 5

Synthesis of Compound D1-4

A compound D1-4 was obtained in the same manner as in Example 1 except that compound A-4 was used instead of compound A-7.

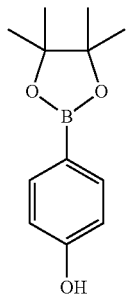

A-4

MALDI-TOF-MASS:
calcd. for C36H24B2N4O4[M+H]+598.20,
FOUND; 598.03

Example 6

Synthesis of Compound D1-5

A compound D1-5 was obtained in the same manner as in Example 1 except that compound A-5 was used instead of compound A-7.

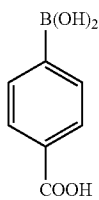

A-5

MALDI-TOF-MASS:
calcd. for C38H24B2N4O6[M+H]+654.19,
FOUND; 653.85

Example 7

Synthesis of Compound D1-8

A compound D1-8 was obtained in the same manner as in Example 1 except that compound A-8 was used instead of compound A-7.

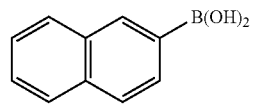

A-8

MALDI-TOF-MASS:
calcd. for C44H28B2N4O2[M+H]+666.24,
FOUND; 666.14

Example 8

Synthesis of Compound D1-9

A compound D1-9 was obtained in the same manner as in Example 1 except that compound A-9 was used instead of compound A-7.

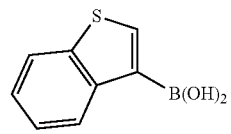

A-9

MALDI-TOF-MASS:
calcd. for C40H24B2N4O2S2[M+H]+678.15,
FOUND; 677.92

Example 9

Synthesis of Compound D1-10

A compound D1-10 was obtained in the same manner as in Example 1 except that compound A-10 was used instead of compound A-7.

A-10

MALDI-TOF-MASS:
calcd. for C32H32B2N4O2[M+H]+526.27,
FOUND; 525.96

Example 10

Synthesis of Compound D2-7

A compound D2-7 was obtained in the same manner as in Example 1 except that 8-amino-1-naphthol was used instead of 1,8-diaminonaphthalene.
MALDI-TOF-MASS:
calcd. for $C_{44}H_{26}B_2N_2O_4[M+H]^+$ 668.21,
FOUND; 667.87

Example 11

Synthesis of Compound D4-7

A compound D4-7 was obtained in the same manner as in Example 1 except that N,N'-dimethyl-1,8-diaminonaphthalene was used instead of 1,8-diaminonaphthalene.
MALDI-TOF-MASS:
calcd. for $C_{48}H_{36}B_2N_4O_2[M+H]^+$ 722.30,
FOUND; 722.19

Comparative Example 1

The following compound was synthesized according to the method disclosed in Japanese Patent No. 3590694.

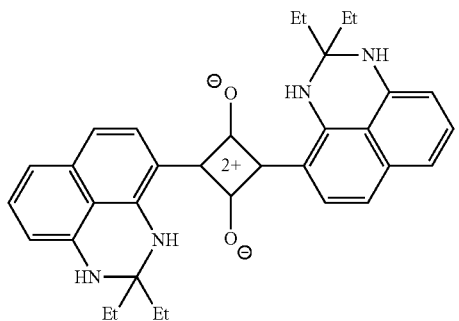 [SMILES: CCC1(CC)Nc2cccc3ccc(C4C([O-])C(c5ccc6cccc7c6c5NC(CC)(CC)N7)C4[O-])c(c23)N1]

Solution Absorption Measurement and Solution Absorption Spectrum

A dilute solution of the squarylium compound thus obtained was prepared and an absorption spectrum in a wavelength range from 350 nm to 1000 nm was measured using a spectrophotometer (UV3100: trade name, UV/VIS spectrophotometer manufactured by Shimadzu Corporation). The results are shown in FIG. 1 and Table 1. The solvent used for measurement was tetrahydrofuran and N,N'-dimethylacetoamide.

TABLE 1

| | Solution absorption measurement | | |
|---|---|---|---|
| Compound No. | Maximum absorption wavelength (nm) | Absorption coefficient | Solvent |
| D1-1 | 827 | 137050 | THF |
| D1-2 | 827 | 134740 | THF |
| D1-3 | 826 | 177470 | THF |
| D1-4 | 828 | 140720 | THF |
| D1-5 | 837 | 108810 | DMAc |
| D1-7 | 827 | 102810 | THF |
| D1-8 | 829 | 174340 | THF |
| D1-9 | 836 | 117700 | DMAc |
| D1-10 | 822 | 140100 | THF |
| D2-7 | 808 | 93460 | THF |
| D4-7 | 831 | 94040 | THF |
| Comparative Example 1 | 807 | 163560 | THF |

* "THF" indicates tetrahydrofuran, and "DMAc" indicates N,N-dimethylacetamide.

As apparent from FIG. 1 and Table 1, the compounds of the present invention had maximum absorption wavelength peaks at relatively longer wavelengths, and were capable of absorbing infrared rays having relatively longer wavelengths, as compared to the compound of Comparative Example. In addition, all of the compounds of the invention had absorbance in the visible region (i.e., from 450 nm to 650 nm) of 0.1 or less, when absorbance of maximum absorption wavelength is 1, and exhibited inherent superior invisibility of squarylium pigments.

Preparation of Microparticle Dispersion

First, 10 parts of a squarylium compound and 4 parts of sodium dodecylbenzene sulfonate as a dispersant were mixed. Then, water was added thereto to adjust 500 parts of the total mass. Subsequently, 500 parts of 0.1 mmφ zirconia beads was added thereto, treated in a planetary ball mill at 300 rpm for 5 hours. The resulting dispersion was filtered to separate the beads, thereby obtaining an aqueous dispersion of the squarylium compound.

In addition, the volume average microparticle diameter of the aqueous dispersion was measured using a NANOTRAC UPA microparticle size analyzer (trade name: UPA-EX150, manufactured by NIKKISO CO., LTD.).

Robustness Test of Microparticles Dispersion

Next, 100 parts of water were added to 50 parts of the aqueous dispersion thus obtained and 10 parts of a polyester urethane resin R9660 (trade name, manufactured by Kusumoto Chemicals, Ltd.), followed by stirring to prepare an aqueous ink. The aqueous ink thus prepared was coated on a commercially-available photo matt paper sheet using a bar coater No. 3, to obtain a coating sample.

The coating sample was set on a 170000 lux xenon discoloration tester equipped with a filter for cutting light of 320 nm or less, and irradiated with light for 24 hours. The variation (difference) in absorbance at maximum absorption wavelengths before and after the irradiation was measured, and the residual ratio of pigments was calculated. The calculation of residual ratio was performed according to the following equation:

Residual ratio=(absorbance after irradiation)/(absorbance before irradiation)×100

The results are shown in Table 2.

TABLE 2

| Compound No. | Average diameter (nm) | Light-robustness of coating sample (residual ratio: %) |
|---|---|---|
| D1-1 | 446 | 54 |
| D1-2 | 344 | 95 |
| D1-4 | 51.1 | 77 |
| D1-5 | 111 | 92 |
| D1-7 | 240 | 97 |
| D1-8 | 481 | 66 |

TABLE 2-continued

| Compound No. | Average diameter (nm) | Light-robustness of coating sample (residual ratio: %) |
|---|---|---|
| D1-9 | 172 | 52 |
| D1-10 | 60.8 | 39 |
| Comp. Ex. 1 | 15.2 | 4 |

As apparent from Table 2, the compounds of the invention had relatively higher residual ratios and thus exhibited superior light-robustness, as compared to the compound of Comparative Example.

What is claimed is:

1. A squarylium compound represented by the following Formula (1):

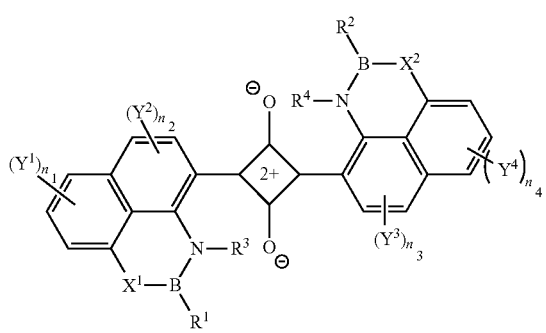

(1)

wherein, in Formula (1), $R^1$ and $R^2$ each independently represent an alkyl group having 1 to 12 carbon atoms, a cycloalkyl group having 3 to 6 carbon atoms, an aryl group of which the number of ring-forming atoms is from 5 to 14, or a heteroaryl group of which the number of ring-forming atoms is from 5 to 14;

wherein the alkyl group, cycloalkyl group, aryl group, and heteroaryl group may independently be substituted by an alkyl group having 1 to 8 carbon atoms, an alkoxy group having 1 to 8 carbon atoms, a hydroxyl group, a carboxyl group, a carbamoyl group, a halogen atom, an alkyloxycarbonyl group having 2 to 7 carbon atoms, an aryloxycarbonyl group having 7 to 11 carbon atoms, an alkylcarbonyloxy having 2 to 7 carbon atoms, an arylcarbonyloxy group having 7 to 11 carbon atoms, an alkylcarbamoyl group having 2 to 7 carbon atoms, or an arylcarbamoyl group having 7 to 11 carbon atoms;

$R^3$ and $R^4$ each independently represent a hydrogen atom or an alkyl group having 1 to 4 carbon atoms;

$X^1$ and $X^2$ each independently represent an oxygen atom or —$NR^5$—, in which $R^5$ represents a hydrogen atom or an alkyl group having 1 to 4 carbon atoms;

$Y^1$, $Y^2$, $Y^3$ and $Y^4$ each independently represent a halogen atom, an alkyl group having 1 to 6 carbon atoms, a cycloalkyl group having 4 to 6 carbon atoms, an aryl group of which the number of ring-forming atoms is from 5 to 14, a heteroaryl group of which the number of ring-forming atoms is from 5 to 14, an arylcarbonyloxy group of which the number of ring-forming atoms is from 5 to 14, or an alkylcarbonyloxy group having 2 to 7 carbon atoms;

when a plurality of $Y^1$'s is present, the plurality of $Y^1$'s may be bonded to each other to form a ring structure;

when a plurality of $Y^2$'s is present, the plurality of $Y^2$'s may be bonded to each other to form a ring structure;

when a plurality of $Y^3$'s is present, the plurality of $Y^3$'s may be bonded to each other to form a ring structure;

when a plurality of $Y^4$'s is present, the plurality of $Y^4$'s may be bonded to each other to form a ring structure;

$Y^1$ and $Y^2$ may be bonded to each other to form a ring structure;

$Y^3$ and $Y^4$ may be bonded to each other to form a ring structure;

$n_1$ and $n_4$ each independently represent an integer of from 0 to 3; and $n_2$ and $n_3$ each independently represent an integer of from 0 to 2.

2. The squarylium compound according to claim 1, wherein $R^3$ and $R^4$ each independently represent a hydrogen atom or a methyl group.

3. The squarylium compound according to claim 1, wherein $n_1$, $n_2$, $n_3$ and $n_4$ each represent zero.

4. The squarylium compound according to claim 1, wherein $X^1$ and $X^2$ each represent an oxygen atom.

5. The squarylium compound according to claim 1, wherein $X^1$ and $X^2$ each represent —NH— or —$NCH_3$—.

6. A microparticle comprising the squarylium compound according to claim 1.

7. A coating composition comprising the microparticle according to claim 6.

8. An infrared absorbent comprising the squarylium compound represented by the following Formula (1A):

(1A)

wherein, in Formula (1A), $R^{11}$ and $R^{12}$ each independently represent a substituted or unsubstituted alkyl group, a substituted or unsubstituted cycloalkyl group, a substituted or unsubstituted aryl group, or a substituted or unsubstituted heteroaryl group;

$R^{13}$ and $R^{14}$ each independently represent a hydrogen atom or a substituted or unsubstituted alkyl group;

$X^{11}$ and $X^{12}$ each independently represent an oxygen atom or —$NR^{15}$—, in which $R^{15}$ represents a hydrogen atom or a substituted or unsubstituted alkyl group;

$Y^{11}$, $Y^{12}$, $Y^{13}$ and $Y^{14}$ each independently represent a halogen atom, a substituted or unsubstituted alkyl group, a substituted or unsubstituted cycloalkyl group, a substituted or unsubstituted aryl group, a substituted or unsubstituted heteroaryl group, a substituted or unsubstituted arylcarbonyloxy group, or a substituted or unsubstituted alkylcarbonyloxy group;

when a plurality of $Y^{11}$'s is present, the plurality of $Y^{11}$'s may be bonded to each other to form a ring structure;

when a plurality of $Y^{12}$'s is present, the plurality of $Y^{12}$'s may be bonded to each other to form a ring structure;

when a plurality of $Y^{13}$'s is present, the plurality of $Y^{13}$'s may be bonded to each other to form a ring structure;

when a plurality of $Y^{14}$'s is present, the plurality of $Y^{14}$'s may be bonded to each other to form a ring structure;

$Y^{11}$ and $Y^{12}$ may be bonded to each other to form a ring structure;

$Y^{13}$ and $Y^{14}$ may be bonded to each other to form a ring structure;

$n_{11}$ and $n_{14}$ each independently represent an integer of from 0 to 3; and $n_{12}$ and $n_{13}$ each independently represent an integer of from 0 to 2.

9. A method for producing a squarylium compound represented by the following Formula (1):

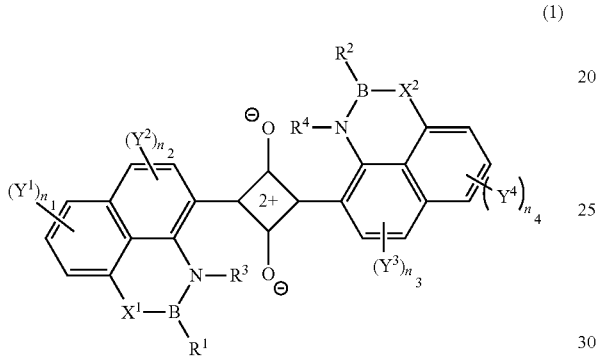

(1)

wherein, in Formula (1), $R^1$ and $R^2$ each independently represent an alkyl group having 1 to 12 carbon atoms, a cycloalkyl group having 3 to 6 carbon atoms, an aryl group of which the number of ring-forming atoms is from 5 to 14, or a heteroaryl group of which the number of ring-forming atoms is from 5 to 14;

wherein the alkyl group, cycloalkyl group, aryl group, and heteroaryl group may independently be substituted by an alkyl group having 1 to 8 carbon atoms, an alkoxy group having 1 to 8 carbon atoms, a hydroxyl group, a carboxyl group, a carbamoyl group, a halogen atom, an alkyloxycarbonyl group having 2 to 7 carbon atoms, an aryloxycarbonyl group having 7 to 11 carbon atoms, an alkylcarbonyloxy group having 2 to 7 carbon atoms, an arylcarbonyloxy group having 7 to 11 carbon atoms, an alkylcarbamoyl group having 2 to 7 carbon atoms, or an arylcarbamoyl group having 7 to 11 carbon atoms;

$R^3$ and $R^4$ each independently represent a hydrogen atom or an alkyl group having 1 to 4 carbon atoms;

$X^1$ and $X^2$ each independently represent an oxygen atom or —$NR^5$—, in which $R^5$ represents a hydrogen atom or an alkyl group having 1 to 4 carbon atoms;

$Y^1$, $Y^2$, $Y^3$ and $Y^4$ each independently represent a halogen atom, an alkyl group having 1 to 6 carbon atoms, a cycloalkyl group having 4 to 6 carbon atoms, an aryl group of which the number of ring-forming atoms is from 5 to 14, a heteroaryl group of which the number of ring-forming atoms is from 5 to 14, an arylcarbonyloxy group of which the number of ring-forming atoms is from 5 to 14, or an alkylcarbonyloxy group having 2 to 7 carbon atoms;

when a plurality of $Y^1$'s is present, the plurality of $Y^1$'s may be bonded to each other to form a ring structure;

when a plurality of $Y^2$'s is present, the plurality of $Y^2$'s may be bonded to each other to form a ring structure;

when a plurality of $Y^3$'s is present, the plurality of $Y^3$'s may be bonded to each other to form a ring structure;

when a plurality of $Y^4$'s is present, the plurality of $Y^4$'s may be bonded to each other to form a ring structure;

$Y^1$ and $Y^2$ may be bonded to each other to form a ring;

$Y^3$ and $Y^4$ may be bonded to each other to form a ring;

$n_1$ and $n_4$ each independently represent an integer of from 0 to 3; and $n_2$ and $n_3$ each independently represent an integer of from 0 to 2, the method comprising:
reacting a compound represented by the following Formula (2) and a compound represented by the following Formula (3) with squaric acid:

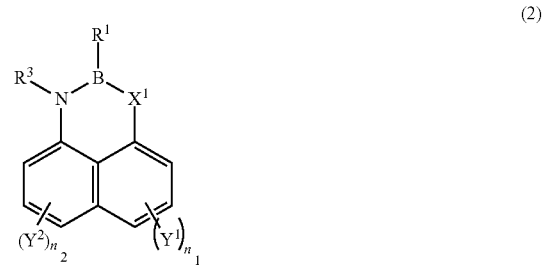

(2)

wherein, in Formula (2), $R^1$, $R^3$, $X^1$, $Y^1$, $Y^2$, $n_1$ and $n_2$ have the same definitions as those of Formula (1), respectively;

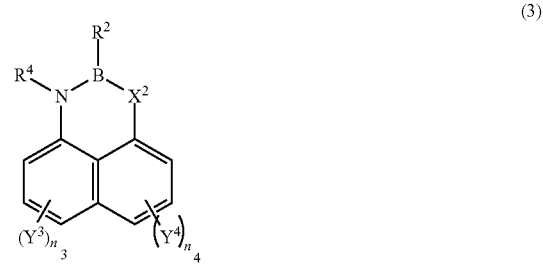

(3)

wherein, in Formula (3), $R^2$, $R^4$, $X^2$, $Y^3$, $Y^4$, $n_3$ and $n_4$ have the same definitions as those of Formula (1), respectively.

10. The method according to claim 9, wherein the compound represented by Formula (3) is the same as the compound represented by Formula (2).

11. The method according to claim 9, further comprising:
producing the compound represented by Formula (2) by reacting a boronic acid compound represented by the following Formula (5) with a 1,8-diaminonaphthalene compound or a 1-amino-8-hydroxynaphthalene compound:

(5)

wherein, in Formula (5), $R^1$ has the same definition as that of Formula (2); and R's each independently represent a hydrogen atom, or an alkyl group having 1 to 3 carbon atoms, and R's may be bonded to each other to form a ring structure.

* * * * *